(12) United States Patent
Deshayes et al.

(10) Patent No.: US 9,115,238 B2
(45) Date of Patent: Aug. 25, 2015

(54) SWELLABLE SYNTHETIC MICROCARRIERS FOR CULTURING CELLS

(75) Inventors: Sophie Deshayes, Rampillon (FR); David Henry, Moribny-Champigny (FR); Martial Hervy, Thomery (FR)

(73) Assignee: Corning Incorporated, Corning, NY (US)

(*) Notice: Subject to any disclaimer, the term of this patent is extended or adjusted under 35 U.S.C. 154(b) by 567 days.

(21) Appl. No.: 12/788,917

(22) Filed: May 27, 2010

(65) Prior Publication Data

US 2010/0304482 A1 Dec. 2, 2010

Related U.S. Application Data

(60) Provisional application No. 61/181,776, filed on May 28, 2009.

(51) Int. Cl.
| | |
|---|---|
| C08F 210/00 | (2006.01) |
| C08F 251/00 | (2006.01) |
| C08F 289/00 | (2006.01) |
| C08F 2/32 | (2006.01) |
| C08F 220/26 | (2006.01) |
| C12N 5/00 | (2006.01) |
| C12N 5/0735 | (2010.01) |
| C08F 222/16 | (2006.01) |
| C08F 222/38 | (2006.01) |

(52) U.S. Cl.
CPC .............. *C08F 289/00* (2013.01); *C08F 2/32* (2013.01); *C08F 220/26* (2013.01); *C12N 5/0075* (2013.01); *C12N 5/0606* (2013.01); *C08F 222/16* (2013.01); *C08F 222/38* (2013.01); *C12N 2531/00* (2013.01); *C12N 2533/30* (2013.01); *C12N 2533/50* (2013.01)

(58) Field of Classification Search
CPC . C12N 2533/30; C08F 210/00; C08F 251/00; C08F 2216/00; C08F 2500/14; C08F 2800/20
See application file for complete search history.

(56) References Cited

U.S. PATENT DOCUMENTS

| | | | |
|---|---|---|---|
| 4,070,348 A | 1/1978 | Kraemer et al. | |
| 5,015,576 A | 5/1991 | Nilsson et al. | |
| 5,994,475 A * | 11/1999 | Roth et al. | 525/326.7 |
| 2006/0127878 A1 | 6/2006 | Salomon et al. | |
| 2009/0191627 A1 | 7/2009 | Fadeev et al. | |
| 2009/0191632 A1 | 7/2009 | Fadeev et al. | |

FOREIGN PATENT DOCUMENTS

| | | |
|---|---|---|
| WO | 8905150 | 6/1989 |
| WO | 2006/105278 | 10/2006 |
| WO | 2008/083390 | 7/2008 |

OTHER PUBLICATIONS

Kim et al, Biotechnol. Prog. 18:495-500, 2002.*
Phillips et al, J. Biotechnol. 138: 24-32, 2008; available online Aug. 14, 2008.*
Faxalv et al, Acta Biomaterialia 6:2599-2608, 2010.*
Santa Cruz Biotech, http://222.scbt.com/datasheet-254190-2-carboxyethyl-acrylate.html; accessed Aug. 16, 2012.*
Liu et al, J. Biomater. Sci. Polymer Edn. 19(6):821-835, 2008.*
Koide et al, Syntheses and Biological Activities of Selenium Analogs of oc-Rat Atrial Natriuretic Peptide, 1993, Chem. Phann. Bull. 41(3):502-6.
Koide et al, Synthetic Study on Selenocystine-Containing Peptides, 1993, Chem. Pharm. Bull. 41(9):1596-1600.
Besse and Moroder, Synthesis of Selenocysteine Peptides and their Oxidation to Diselenide-bridged Compounds, 1997, Journal of Peptide Science, vol. 3, 442-453.
Thompson, Embryonic Stem Cell Lines Derived from Human Blastocysts, (1998) Science 282; pp. 1145-1147.
Genbacev et al., Serum-free derivation of human embryonic stem cell lines on human placental fibroblast feeders, Fertil. Steril. 83(5):1517-29, 2005.
Klimanskaya et al., Human embryonic stem cells derived without feeder cells, Lancet, 365(9471):1636-41, 2005.
Takahashi et al., Induction of Pluripotent Stem Cells from Adult Human Fibroblasts by Defined Factors, (2007) Cell 131 (5) pp. 861-872.
Yu et al., Induced Pluripotent Stem Cell Lines Derived from Human Somatic Cells, (2007) Science318:pp. 1917-1920.
Horak et al., Biomaterials. Oct. 2004;25(22):5249-60. Poly(2-hydroxyethyl methacrylate)-based slabs as a mouse embryonic stem cell support.
Fernandez et al. "Mouse embryonic stem cell expansion in a Microcarrier-based stirred culture system", J Biotechnol. Oct. 31, 2007;132(2):227-36. Epub Jun. 7, 2007.
Nie et al Biotechnol Prog. Jan.-Feb. 2009;25(1):20-31. "Scalable culture and cryopreservation of human embryonic stem cells on Microcarriers".
Abranches et al., Biotechnol Bioeng. Apr. 15, 2007;96(6):1211-21, "Expansion of mouse embryonic stem cells on Microcarriers".
"Bioreactor development for stem cell expansion and controlled differentiation", Curr Opin Chem Biol. Aug. 2007;11(4):394-8. Epub Jul. 25, 2007, King et al.
"Inverse Suspension Polymerization of sodium Acrylate: Synthesis and Characterization", Mayoux et al, Journal of applied polymer science, vol. 77, 2621-2630 (2000).
Vianna-Soares et al.,"HPMA and HEMA Copolymer Bean Interactions with Eukaryotic Cells", Materials Research. 2004, 7 (3), 473-77.
Zecheru et al., "New hema-based polymeric microbeads for drug delivery systems", J. Optoelect. Advan. Mat. 2006, 8(3), 1312-16.

\* cited by examiner

*Primary Examiner* — Kevin Hill
(74) *Attorney, Agent, or Firm* — Susan S. Wilks; Keith Campbell

(57) ABSTRACT

A cell culture microcarrier includes a polymer formed from copolymerization of a mixture including (i) an uncharged hydrophilic unsaturated monomer having a hydroxyl group; (ii) a hydrophilic carboxylic acid containing unsaturated monomer; and (iii) a hydrophilic multifunctional unsaturated monomer. The microcarrier may further include a polypeptide, such as a polypeptide that promotes cell adhesion, conjugated to the surface of the microcarrier; e.g. via the carboxyl group from the hydrophilic carboxylic acid containing unsaturated monomer. Some of the microcarriers support attachment of human embryonic stem cells.

21 Claims, 15 Drawing Sheets

```
SEQUENCE LISTING

<160> NUMBER OF SEQ ID NOS: 26

<210> SEQ ID NO 1
<211> LENGTH: 15
<212> TYPE: PRT
<213> ORGANISM: Artificial Sequence
<220> FEATURE:
<223> OTHER INFORMATION: polypeptide

<400> SEQUENCE: 1

Lys Gly Gly Asn Gly Glu Pro Arg Gly Asp Thr Tyr Arg Ala Tyr
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: polypeptide

<400> SEQUENCE: 2

Asn Gly Glu Pro Arg Gly Asp Thr Tyr Arg Ala Tyr
1               5                   10

<210> SEQ ID NO 3
<211> LENGTH: 7
<212> TYPE: PRT
<213> ORGANISM: Artificial Sequence
<220> FEATURE:
<223> OTHER INFORMATION: polypeptide

<400> SEQUENCE: 3

Gly Arg Gly Asp Ser Pro Lys
1               5
```

```
<210> SEQ ID NO 4
<211> LENGTH: 12
<212> TYPE: PRT
<213> ORGANISM: Artificial Sequence
<220> FEATURE:
<223> OTHER INFORMATION: polypeptide

<400> SEQUENCE: 4

Ala Val Thr Gly Arg Gly Asp Ser Pro Ala Ser Ser
1               5                   10

<210> SEQ ID NO 5
<211> LENGTH: 12
<212> TYPE: PRT
<213> ORGANISM: Artificial Sequence
<220> FEATURE:
<223> OTHER INFORMATION: polypeptide

<400> SEQUENCE: 5

Pro Gln Val Thr Arg Gly Asp Val Phe Thr Met Pro
1               5                   10

<210> SEQ ID NO 6
<211> LENGTH: 10
<212> TYPE: PRT
<213> ORGANISM: Artificial Sequence
<220> FEATURE:
<223> OTHER INFORMATION: polypeptide

<400> SEQUENCE: 6

Arg Asn Ile Ala Glu Ile Ile Lys Asp Ile
1               5                   10

<210> SEQ ID NO 7
<211> LENGTH: 15
<212> TYPE: PRT
<213> ORGANISM: Artificial Sequence
<220> FEATURE:
<223> OTHER INFORMATION: polypeptide

<400> SEQUENCE: 7

Lys Tyr Gly Arg Lys Arg Leu Gln Val Gln Leu Ser Ile Arg Thr
1               5                   10                  15

<210> SEQ ID NO 8
<211> LENGTH: 11
<212> TYPE: PRT
<213> ORGANISM: Artificial Sequence
<220> FEATURE:
<223> OTHER INFORMATION: polypeptide

<400> SEQUENCE: 8

Asn Gly Glu Pro Arg Gly Asp Thr Arg Ala Tyr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: polypeptide

<400> SEQUENCE: 9

Asn Gly Glu Pro Arg Gly Asp Thr Tyr Arg Ala Tyr
1               5                   10
```

<210> SEQ ID NO 10
<211> LENGTH: 15
<212> TYPE: PRT
<213> ORGANISM: Artificial Sequence
<220> FEATURE:
<223> OTHER INFORMATION: polypeptide

<400> SEQUENCE: 10

Lys Tyr Gly Ala Ala Ser Ile Lys Val Ala Val Ser Ala Asp Arg
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: polypeptide

<400> SEQUENCE: 11

Lys Tyr Gly Lys Ala Phe Asp Ile Thr Tyr Val Arg Leu Lys Phe
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: polypeptide

<400> SEQUENCE: 12

Lys Tyr Gly Ser Glu Thr Thr Val Lys Tyr Ile Phe Arg Leu His Glu
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: polypeptide

<400> SEQUENCE: 13

Lys Tyr Gly Thr Asp Ile Arg Val Thr Leu Asn Arg Leu Asn Thr Phe
1               5                   10                  15

<210> SEQ ID NO 14
<211> LENGTH: 12
<212> TYPE: PRT
<213> ORGANISM: Artificial Sequence
<220> FEATURE:
<223> OTHER INFORMATION: Polypeptide

<400> SEQUENCE: 14

Thr Ser Ile Lys Ile Arg Gly Thr Tyr Ser Glu Arg
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Polypeptide

<400> SEQUENCE: 15

Thr Trp Tyr Lys Ile Ala Phe Gln Arg Asn Arg Lys
1               5                   10

```
<210> SEQ ID NO 16
<211> LENGTH: 20
<212> TYPE: PRT
<213> ORGANISM: Artificial Sequence
<220> FEATURE:
<223> OTHER INFORMATION: Polypeptide

<400> SEQUENCE: 16

Ser Ile Asn Asn Asn Arg Trp His Ser Ile Tyr Ile Thr Arg Phe Gly
1               5                   10                  15

Asn Met Gly Ser
            20

<210> SEQ ID NO 17
<211> LENGTH: 13
<212> TYPE: PRT
<213> ORGANISM: Artificial Sequence
<220> FEATURE:
<223> OTHER INFORMATION: Polypeptide

<400> SEQUENCE: 17

Lys Tyr Gly Leu Ala Leu Glu Arg Lys Asp His Ser Gly
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Polypeptide

<400> SEQUENCE: 18

Gly Gln Lys Cys Ile Val Gln Thr Thr Ser Trp Ser Gln Cys Ser Lys
1               5                   10                  15

Ser

<210> SEQ ID NO 19
<211> LENGTH: 17
<212> TYPE: PRT
<213> ORGANISM: Artificial Sequence
<220> FEATURE:
<223> OTHER INFORMATION: Polypeptide
<220> FEATURE:
<221> NAME/KEY: MISC_FEATURE
<222> LOCATION: (4)..(4)
<223> OTHER INFORMATION: Lysine at residue 4 forms amide bond with
      Aspartic Acid at residue 17 to cyclize the polypeptide
<220> FEATURE:
<221> NAME/KEY: MISC_FEATURE
<222> LOCATION: (17)..(17)
<223> OTHER INFORMATION: Aspartic Acid at residue 17 forms amide bond
      with Lysine at residue 4 to cyclize the polypeptide

<400> SEQUENCE: 19

Lys Gly Gly Lys Asp Gly Glu Pro Arg Gly Asp Thr Tyr Arg Ala Thr
1               5                   10                  15

Asp

<210> SEQ ID NO 20
<211> LENGTH: 13
<212> TYPE: PRT
<213> ORGANISM: Artificial Sequence
<220> FEATURE:
<223> OTHER INFORMATION: Polypeptide
<220> FEATURE:
<221> NAME/KEY: MISC_FEATURE
<222> LOCATION: (4)..(4)
<223> OTHER INFORMATION: Leucine at residue 4 forms amide bond with
```

Aspartic Acid at residue 13 to cyclize the polypeptide
<220> FEATURE:
<221> NAME/KEY: MISC_FEATURE
<222> LOCATION: (13)..(13)
<223> OTHER INFORMATION: Aspartic Acid at residue 13 forms amide bond
      with Leucine at residue 4 to cyclize the polypeptide

<400> SEQUENCE: 20

Lys Gly Gly Leu Glu Pro Arg Gly Asp Thr Tyr Arg Asp
1               5                   10

<210> SEQ ID NO 21
<211> LENGTH: 17
<212> TYPE: PRT
<213> ORGANISM: Artificial Sequence
<220> FEATURE:
<223> OTHER INFORMATION: Polypeptide
<220> FEATURE:
<221> NAME/KEY: MISC_FEATURE
<222> LOCATION: (4)..(4)
<223> OTHER INFORMATION: Cysteine at residue 4 forms a disulfide bond
      with Cysteine at residue 17 to cyclize the polypeptide
<220> FEATURE:
<221> NAME/KEY: MISC_FEATURE
<222> LOCATION: (17)..(17)
<223> OTHER INFORMATION: Cysteine at residue 17 forms a disulfide bond
      with Cysteine at residue 4 to cyclize the polypeptide

<400> SEQUENCE: 21

Lys Gly Gly Cys Asn Gly Glu Pro Arg Gly Asp Thr Tyr Arg Ala Thr
1               5                   10                  15

Cys

<210> SEQ ID NO 22
<211> LENGTH: 13
<212> TYPE: PRT
<213> ORGANISM: Artificial Sequence
<220> FEATURE:
<223> OTHER INFORMATION: Polypeptide
<220> FEATURE:
<221> NAME/KEY: MISC_FEATURE
<222> LOCATION: (4)..(4)
<223> OTHER INFORMATION: Cysteine at residue 4 forms a disulfide bond
      with Cysteine at residue 13 to cyclize the polypeptide
<220> FEATURE:
<221> NAME/KEY: MISC_FEATURE
<222> LOCATION: (13)..(13)
<223> OTHER INFORMATION: Cysteine at residue 13 forms a disulfide bond
      with Cysteine at residue 4 to cyclize the polypeptide

<400> SEQUENCE: 22

Lys Gly Gly Cys Glu Pro Arg Gly Asp Thr Tyr Arg Cys
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Polypeptide

<400> SEQUENCE: 23

Lys Gly Gly Ala Val Thr Gly Asp Gly Asn Ser Pro Ala Ser Ser
1               5                   10                  15

<210> SEQ ID NO 24
<211> LENGTH: 15
<212> TYPE: PRT
<213> ORGANISM: Artificial Sequence
<220> FEATURE:

```
<223> OTHER INFORMATION: Polypeptide

<400> SEQUENCE: 24

Lys Gly Gly Pro Gln Val Thr Arg Gly Asp Val Phe Thr Met Pro
1               5                   10                  15

<210> SEQ ID NO 25
<211> LENGTH: 9
<212> TYPE: PRT
<213> ORGANISM: Artificial Sequence
<220> FEATURE:
<223> OTHER INFORMATION: Polypeptide

<400> SEQUENCE: 25

Gly Arg Gly Glu Ser Pro Ile Ile Lys
1               5

<210> SEQ ID NO 26
<211> LENGTH: 5
<212> TYPE: PRT
<213> ORGANISM: Artificial Sequence
<220> FEATURE:
<223> OTHER INFORMATION: Polypeptide

<400> SEQUENCE: 26

Gly Arg Gly Asp Ser
1               5
```

SWELLABLE SYNTHETIC MICROCARRIERS FOR CULTURING CELLS

CLAIMING BENEFIT OF PRIOR FILED U.S. APPLICATION

This application claims the benefit of U.S. Provisional Application Ser. No. 61/181,776 filed on May 28, 2009. The content of this document and the entire disclosure of publications, patents, and patent documents mentioned herein are incorporated by reference.

FIELD

The present disclosure relates to cell culture microcarriers, and more particularly to synthetic, chemically-defined microcarriers.

SEQUENCE LISTING

This application contains a Sequence Listing electronically submitted via EFS-Web to the United States Patent and Trademark Office as text filed named "SP10173_ST25.txt" having a size of 8 kb and created on May 27, 2010. Due to the electronic filing of the Sequence Listing, the electronically submitted Sequence Listing serves as both the paper copy required by 37 CFR §1.821(c) and the CRF required by §1.821(e). The information contained in the Sequence Listing is hereby incorporated herein by reference.

BACKGROUND

Microcarriers have been employed in cell culture for the purpose of providing high yields of attachment-dependent cells. Microcarriers are typically stirred or agitated in cell culture media and provide a very large attachment and growth surface area to volume ratio relative to more traditional culture equipment.

Most currently available microcarriers provide for non-specific attachment of cells to the carriers for cell growth. While useful, such microcarriers do not allow for biospecific cell adhesion and thus do not readily allow for tailoring of characteristics of the cultured cells. For example, due to non-specific interactions it may be difficult to maintain cells, such as stem cells, in a particular state of differentiation or to direct cells to differentiate in a particular manner.

Some currently available microcarriers provide for bio-specific adhesion, but employ animal derived coating such as collagen or gelatin. Such animal derived coatings can expose the cells to potentially harmful viruses or other infectious agents which could be transferred to patients if the cells are used for a therapeutic purpose. In addition, such viruses or other infectious agents may compromise general culture and maintenance of the cultured cells. Further, such biological products tend to be vulnerable to batch variation and limited shelf-life.

BRIEF SUMMARY

Among other things, the present disclosure described synthetic, chemically-defined microcarriers useful in culturing cells. The microcarriers described herein are, in various embodiments, durable enough to withstand stirring while maintaining cell adhesion and growth, even though the microspheres may be highly swellable.

In various embodiments, a microcarrier includes a polymer formed from copolymerization of a mixture including (i) an uncharged hydrophilic unsaturated monomer having a hydroxyl group; (ii) a hydrophilic carboxylic acid containing unsaturated monomer; and (iii) a hydrophilic multifunctional unsaturated monomer. The microcarrier may further include a polypeptide, such as a polypeptide that promotes cell adhesion, conjugated to the surface of the microcarrier; e.g. via the carboxyl group from the hydrophilic carboxylic acid containing unsaturated monomer. Preferably, the polymeric base does not allow for non-specific adhesion of cells, and the polypeptide provides for bio-specific cell binding.

In various embodiments, a method for producing a cell culture microcarrier includes copolymerizing a mixture of monomers to form the microcarrier base. The mixture of monomers includes (i) an uncharged hydrophilic unsaturated monomer having a hydroxyl group; (ii) a hydrophilic carboxylic acid containing unsaturated monomer; and (iii) a hydrophilic multifunctional unsaturated monomer. In some embodiments, the mixture of monomers is copolymerized by water-in-oil copolymerization. The method further includes conjugating a polypeptide to the microcarrier base to form the microcarrier.

In numerous embodiments, a method for culturing cells includes contacting the cells with a cell culture medium having microcarriers. The microcarriers include a polymeric base formed from a mixture of monomers including (i) an uncharged hydrophilic unsaturated monomer having a hydroxyl group; (ii) a hydrophilic carboxylic acid containing unsaturated monomer; and (iii) a hydrophilic multifunctional unsaturated monomer; and include a polypeptide conjugated polymer. The method further includes culturing the cells in the medium. The cells may be stem cells, such as embryonic stem cells, and the medium may be a chemically defined medium.

One or more of the various embodiments presented herein provide one or more advantages over prior articles and systems for culturing cells. For example, synthetic microcarriers described herein have been shown to support cell adhesion without the need of animal derived biocoating which limits the risk of pathogen contamination. This is especially relevant when cells are dedicated to cell therapies. Further, large scale culture of cells, including human embryonic stem cells (hESCs), is possible with microcarriers as described herein. Such microcarriers may also be advantageously used for culturing cells other than stem cells when the presence of animal derived products such as collagen, gelatin, fibronectin, etc. are undesired or prohibited. The methods described herein allow for the preparation of microcarriers having a wide range of properties such as stiffness, swellability, surface chemistries, and can provide microcarriers having a soft swellable substrate that prevents cell damage when cells are cultured in stirred tanks. Further, the microcarriers may be monolithic and not coated as most of the commercial microcarriers, reducing the number of components to worry about with regard to manufacturing complexity and cell compatibility. These and other advantages will be readily understood from the following detailed descriptions when read in conjunction with the accompanying drawings

DETAILED DESCRIPTION

Figure 1:
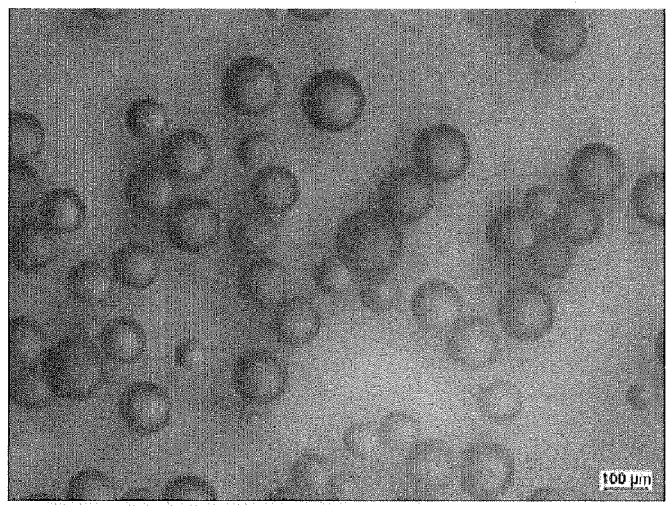
FIG. 1 is microscopic image of representative microcarriers prepared according to Example 1.

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Polypeptide sequences are referred to herein by their one letter amino acid codes and by their three letter amino acid codes. These codes may be used interchangeably.

As used herein, "monomer" means a compound capable of polymerizing with another monomer, (regardless of whether the "monomer" is of the same or different compound than the other monomer), which compound has a molecular weight of less that about 1000 Dalton. In many cases, monomers will have a molecular weight of less than about 400 Dalton.

As used herein, "microcarrier base" means a polymeric microcarrier on which a polypeptide may be conjugated. "Microcarrier base" and "polymeric microcarrier" are often used herein interchangeably. A microcarrer is small discrete particle for use in culturing cells and to which cells may attach. Microcarriers may be in any suitable shape, such as rods, spheres, and the like, and may be porous or non-porous.

As used herein "peptide" and "polypeptide" mean a sequence of amino acids that may be chemically synthesized or may be recombinantly derived, but that are not isolated as entire proteins from animal sources. For the purposes of this disclosure, peptides and polypeptides are not whole proteins. Peptides and polypeptides may include amino acid sequences that are fragments of proteins. For example peptides and polypeptides may include sequences known as cell adhesion sequences such as RGD. Polypeptides may be of any suitable length, such as between three and thirty amino acids in length. Polypeptides may be acetylated (e.g. Ac-LysGlyGly) or amidated (e.g. SerLysSer-$NH_2$) to protect them from being broken down by, for example, exopeptidases. It will be understood that these modifications are contemplated when a sequence is disclosed.

As used herein, a "(meth)acrylate monomer" means a methacrylate monomer or an acrylate monomer. As used herein "(meth)acrylamide monomer" means a methacrylamide or an acrylamide monomer. (Meth)acrylate and (meth)acrylamide monomers have at least one ethylenically unsaturated moiety. "Poly(meth)acrylate", as used herein, means a polymer formed from one or more monomers including at least one (meth)acrylate monomer. "Poly(meth)acrylamide", as used herein, means a polymer formed from one or more monomers including at least one (meth)acrylamide monomer.

As used herein, "equilibrium water content" refers to water-absorbing characteristic of a polymeric material and is defined and measured by equilibrium water content (EWC) as shown by Formula 1:

$$EWC(\%) = [(Wgel - Wdry)/(Wgel)]*100.$$  Formula 1

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. Accordingly, a microcarrier base formed from a mixture of monomers comprising an uncharged hydrophilic unsaturated monomer having a hydroxyl group; a hydrophilic carboxylic acid containing unsaturated monomer; and a hydrophilic multifunctional unsaturated monomer may be formed from a mixture consisting essentially of, or consisting of, an uncharged hydrophilic unsaturated monomer having a hydroxyl group; a hydrophilic carboxylic acid containing unsaturated monomer; and a hydrophilic multifunctional unsaturated monomer.

As used herein, "hydrophilic", as it relates to a monomer, means the monomer separates into the water phase of an oil-in-water emulsion. For example, 95% or more; e.g. 98% or more, of the monomer separates into the water phase. It will be understood that the amount of monomer that will remain in the water phase depends on the components of the emulsion (e.g., components of the oil phase and emulsifier, if any). For example, in many emulsions where the oil phase is silicone oil or a fluorinated solvent, monomers that are not typically considered very hydrophilic, such as ethylene glycol dimethacrylate, may remain dispersed in the water phase (and thus would be considered "hydrophilic" herein). The ability of a monomer to remain in the water phase in an oil-in-water emulsion is important when microcarriers are formed via oil-in-water copolymerization. If the monomer does not remain in the water phase, the ability to form microcarriers may be compromised. Accordingly, in many embodiments, the monomers are at least water-miscible, and are preferably water soluble, to form at least 5 weight percent solutions when dissolved in water. In some embodiments, hydrophilic monomers have an octanol/water partition coefficient of less than 1.9, less than 1.8, less than 1.7, less that 1.6, less than 1.5, or less than 1.4.

The present disclosure describes, inter alia, synthetic microcarriers for culturing cells. In various embodiments, the microcarriers are configured to support proliferation and maintenance of undifferentiated stem cells in chemically defined media.

1. Microcarrier

A microcarrier, as described herein, is formed by polymerization of a mixture of monomers including an uncharged hydrophilic unsaturated monomer having a hydroxyl group, a hydrophilic carboxylic acid containing unsaturated monomer, and a hydrophilic multifunctional unsaturated monomer. In some embodiments, the polymeric base of the microcarrier is formed from a mixture of monomers consisting of, or consisting essentially of an uncharged hydrophilic unsaturated monomer having a hydroxyl group, a hydrophilic carboxylic acid containing unsaturated monomer, and a hydrophilic multifunctional unsaturated monomer.

A. Uncharged Hydrophilic Unsaturated Monomer Having a Hydroxyl Group

Any suitable uncharged hydrophilic unsaturated monomer having a hydroxyl group may be employed. An "uncharged" monomer is a monomer that, when incorporated into a polymeric microcarrier, is free of charged groups under a given cell culture condition. Microcarriers having charged moieties under cell culture conditions can result in non-specific attachment of cells. It is desired, in various embodiments, for cell interaction with a microcarrier to be biospecific and selective to a polypeptide grafted to the microcarrier.

In various embodiments, the uncharged hydrophilic unsaturated monomer having a hydroxyl group is a (meth)acrylate monomer of Formula (I):

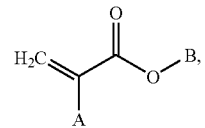

where A is H or methyl, and where B is C1-C6 straight or branched chain alcohol or ether. In some embodiments, B is C1-C4 straight or branched chain alcohol. By way of example, hydroxypropyl methacrylate, 2-hydroxyethyl methacrylate (HEMA), 2-hydroxyethyl acrylate, glycerol methacrylate, hydroxypropyl acrylate, 4-hydroxybutyl acrylate, or the like may be employed.

In various embodiments, the uncharged hydrophilic unsaturated monomer having a hydroxyl group is a (meth)acrylamide monomer of Formula (II):

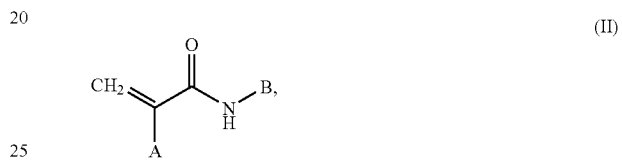

where A is hydrogen or methyl, and where B is C1-C6 straight or branched chain alcohol or ether. In some embodiments, B is C1-C4 straight or branched chain alcohol. For example, the uncharged hydrophilic unsaturated monomer may be N-(hydroxymethyl)acrylamide, N-[Tris(hydroxymethyl)methyl]acrylamide, 3-acryloylamino-1-propanol, N-acrylamidoethoxyethanol, N-hydroxyethyl acrylamide, or the like.

B. Hydrophilic Carboxylic Acid Containing Unsaturated Monomer

Any suitable hydrophilic carboxylic acid containing unsaturated monomer may be employed. In various embodiments, the hydrophilic carboxylic acid containing unsaturated monomer is a (meth)acrylate monomer of Formula (III):

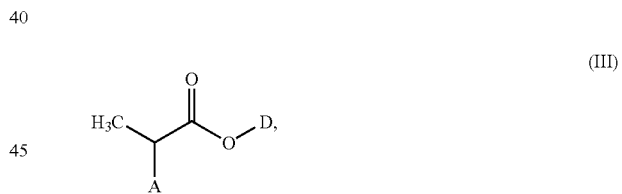

where A is hydrogen or methyl, and where D is C1-C6 straight or branched chain alkyl substituted with a carboxyl group (—COOH). In some embodiments, D is straight or branched chain C1-C3 substituted with a carboxyl group. By way of example, the hydrophilic carboxylic acid containing unsaturated monomer may be 2-carboxyethyl methacrylate, 2-carboxyethyl acrylate, acrylic acid, methacrylic acid or the like.

In various embodiments, the hydrophilic carboxylic acid containing unsaturated monomer is a (meth)acrylamide monomer of Formula (IV):

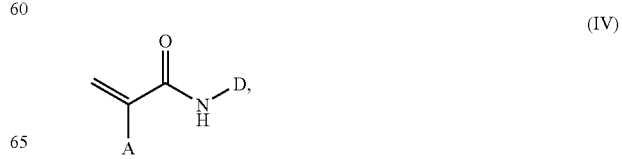

where A is hydrogen or methyl, and where D is C1-C6 straight or branched chain alkyl substituted with a carboxyl group (—COOH). In some embodiments, D is straight or branched chain C1-C3 substituted with a carboxyl group. By way of example, the hydrophilic carboxylic acid containing unsaturated monomer may be 2-carboxyethyl acrylamide, acrylamidoglycolic acid, or the like.

C. Hydrophilic Multifunctional Unsaturated Monomer

Any suitable and a hydrophilic multifunctional unsaturated monomer may be employed. As used herein, "multifunctional monomer" means a monomer having more than one group capable of polymerizing. Multifunctional monomers can serve as cross-linking agents. Multifunctional monomers may be di-, tri-, or higher functions. In various embodiments, multifunctional monomers are difunctional. Multifunctional monomers may have any suitable polymerizable group. In various embodiments, multifunctional monomers have a vinyl group; e.g. a (meth)acrylate group or a (meth)acrylamide group. Examples of suitable multifunctional monomers include N,N' methylenebisacrylamide, N,N'(1,2-dihydroxyethylene)bisacrylamide, polyethylene glycol di(meth)acrylate, triglycerol diacrylate, propylene glycol glycerolate diacrylate, trimethylolpropane ethoxylate triacrylate, glycerol 1,3-diglycerolate diacrylate, and the like.

In various embodiments, the hydrophilic multifunctional unsaturated monomer is more hydrophilic than tetra(ethylene glycol) dimethacrylate. For example, the hydrophilic multifunctional unsaturated monomer may have an octanol/water partition coefficient that is less than the octanol/water coefficient of tetra(ethylene glycol) dimethacrylate. In some embodiments, hydrophilic monomers have an octanol/water partition coefficient of less than 1.9, less than 1.8, less than 1.7, or less that 1.6. In many embodiments, the monomers are at least water-miscible, and are preferably water soluble, to form at least 5 weight percent solutions when dissolved in water.

However, in some embodiments, a hydrophobic or less hydrophilic unsaturated multifunctional monomer is used in addition to the hydrophilic multifunctional unsaturated monomer. For example, tetra(ethylene glycol) dimethacrylate may be employed in addition to a hydrophilic multifunctional unsaturated monomer, such as methylene bisacrylamide (see, e.g., EXAMPLE 17).

D. Formation of Polymeric Microcarrier Base

A microcarrier may be formed via any suitable polymerization reaction of the mixture of monomers. Any suitable amount of an uncharged hydrophilic unsaturated monomer having a hydroxyl group, a hydrophilic carboxylic acid containing unsaturated monomer, and a hydrophilic multifunctional unsaturated monomer may be employed in the mixture. In various embodiments, the mixture of monomers used to form the microcarrier includes (i) about 30 to about 70 parts per weight of the uncharged hydrophilic unsaturated monomer having a hydroxyl group; (ii) about 20 to about 60 parts per weight of the hydrophilic carboxylic acid containing unsaturated monomer; and (iii) 1 to 15 parts by weight of the hydrophilic multifunctional unsaturated monomer. Or, in embodiments, the mixture of monomers used to form the microcarrier includes (i) about 30 to about 70, about 30 to about 60, about 30 to about 55, about 30 to about 50, about 30 to about 45 or about 30 to about 40 parts per weight of the uncharged hydrophilic unsaturated monomer having a hydroxyl group; (ii) more than 20, about 20 to about 60, about 30 to about 60, about 35 to about 60, about 40 to about 60, about 45 to about 60 or about 50 to about 60 per weight of the hydrophilic carboxylic acid containing unsaturated monomer; and (iii) about 1 to 15 or about 1 to about 10 parts by weight of the hydrophilic multifunctional unsaturated monomer. Although the word "about" is used to describe these ranges, it will be understood that these ranges are defined, and can be understood to include or to not include the word "about". As discussed above, a hydrophilic multifunctional unsaturated monomer (e.g., methylene bisacrylamide or dihydroethylene bisacrylamide) may be used in combination with a less hydrophilic or hydrophobic unsaturated monomer (e.g., tetra(ethylene glycol) dimethacrylate). In many of such embodiments, the total crosslinker (multifunctional unsaturated monomer) does not exceed 15 parts by weight of the mixture of monomers, with the more hydrophilic multifunctional unsaturated monomer being at least 1% by weight of the mixture of monomers. The weight percentages of multifunctional unsaturated monomer are particularly well suited for difunctional monomers. It will be understood that the ratio of crosslinker employed may be readily changed (e.g., reduced) if tri- or higher functional monomers are used as crosslinkers.

Figure 19:
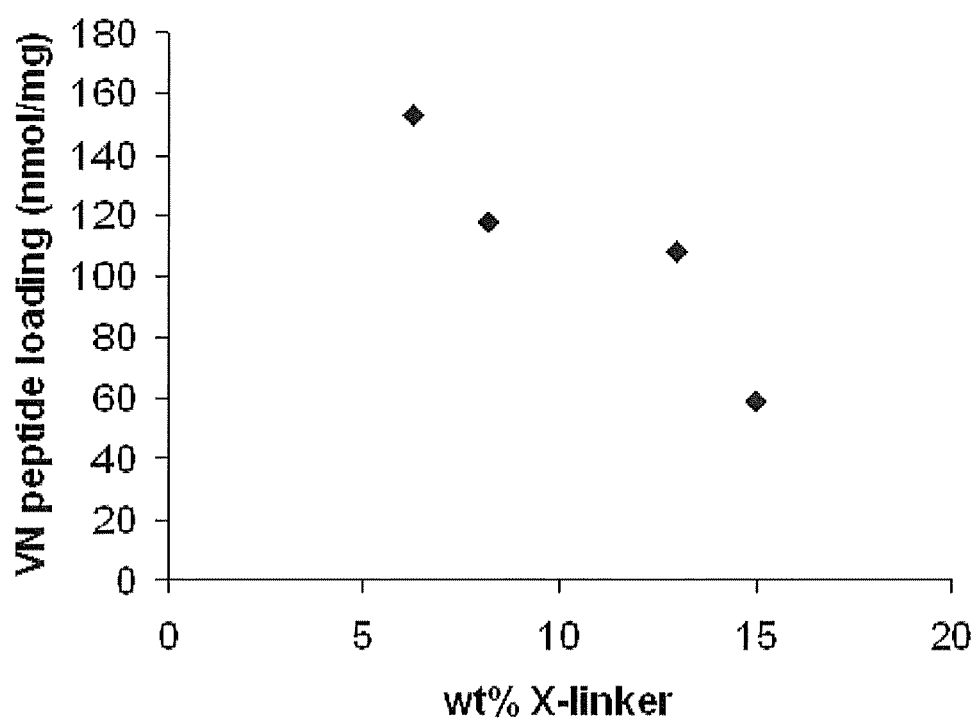
FIG. 19 is a graph illustrating the relationship between VN peptide loading (in nmol/mg) vs weight percent of crosslinker.

The ratio of cross-linker may be changed. For example, as shown in FIG. 19, the percentage of cross-linker employed may affect the peptide loading on the microcarrier. For example, a higher cross-linker weight percent is correlated with a lower loading on the microcarriers. In addition, the cross-linker ratio may also affect the EWC of the microcarrier.

In various embodiments, the pendant carboxyl content (from the hydrophilic carboxylic acid containing unsaturated monomer) of the polymeric microcarrier is greater than about 1 milliequivalents per gram, greater than about 2 milliequivalents per gram, greater than about 3 milliequivalents per gram, or about 4 milliequivalents per gram. In various embodiments, the cross-linking density (from the hydrophilic multifunctional unsaturated monomer) of the polymeric microcarrier is between about $1 \times 10^{-4}$ and $5 \times 10^{-3}$ moles per gram, between about $1.5 \times 10^{-3}$ and $2.5 \times 10^{-3}$ moles per gram, or about $1.7 \times 10^{-3}$ moles per gram.

It will be understood that the relative amounts of the monomers and the properties of the monomers will affect the desired properties of the resulting polymeric microcarrier. For example, it will be understood that the equilibrium water content (EWC) of the polymeric microcarrier may be controlled by the monomers chosen to form the microcarrier. For example, a higher degree of hydrophilicity of the monomers used, the higher the EWC of the polymeric microcarrier will be. However, this may be attenuated by increasing the percentage, or increasing the functionality, of the cross-linking monomer (the hydrophilic multifunctional unsaturated monomer), which should reduce the ability of the SA layer to swell and thereby reduce the EWC. While not intending to be bound by theory, it is believed that the EWC of the polymeric microcarrier may be an important variable in determining what types of cells the microcarrier can support in culture. The stiffness and swelling power of the microcarrier may mimic environments in which certain cells grow well. As presented in co-pending patent applications, U.S. patent application Ser. Nos. 12/362,924 and 12/362,974, swellable surface layers having an EWC of between about 5% and about 70% were suitable for culturing human embryonic stem cells in an undifferentiated state for at least five passages. In these copending applications, the swellable (meth)acrylate layers were formed in situ on a substrate. If the EWC were too high, the layer may swell too much when exposed to an aqueous environment such as cell culture and delaminate. However, as the microcarriers described herein are not formed as a layer on a substrate, delamination is not a concern and the EWC can be higher. In many respects, microcarriers with higher EWCs are desirable because they tend to have low stiffness and thus more closely resemble biological tissue stiffness. They are "soft" surfaces. They may also have high transparency due to the high amount of water, and prevent or reduce cell damage during collision in stirred cultures. However, if the microcarriers are too soft, they may be difficult to handle or may aggregate and thus may be difficult to disperse in culture medium. By adjusting the crosslinker percentage, and the chemical nature of the crosslinker, the EWC can be "tuned."

While microcarriers as described herein can have any suitable EWC, in various embodiments, a microcarrier as described herein has an EWC of greater than about 60%, greater than about 65%, greater than about 70%, greater than about 75%, greater than about 80%, greater than about 85%, or greater than about 90%. Due in part to the use of a carboxyl containing monomer in the microcarriers of various embodiments described herein, the EWC may be pH dependent. For example, the EWC of particular microcarriers may be higher in phosphate buffer (pH 7.4) than in distilled, deionized water (pH ~5). In various embodiments, the EWC of a microcarrier in distilled, deionized water is greater than about 60%, greater than about 65%, greater than about 70%, greater than about 75%, greater than about 80%, greater than about 85%, or greater than about 90%

As discussed further below, one or more polypeptides may be conjugated to microcarrier, which may affect the EWC of the microcarrier (typically increasing the EWC). The amount of polypeptide conjugated to a microcarrier tends to be variable and can change depending on the size (e.g., diameter) of the microcarrier. Accordingly, the EWC of microcarrier with conjugated polypeptide prepared in accordance with a standard protocol may be variable. For purposes of reproducibility, it may be desirable to measure the EWC of microcarriers prior to conjugation with a polypeptide. With this noted, in some embodiments, after the microcarriers have been conjugated with polypeptides, the EWC of embodiments of microcarrier-polypeptide conjugates may be greater than about 50%, greater than about 55%, greater than about 60%, greater than about 65%, greater than about 70%, greater than about 75%, greater than about 80%, greater than about 85%, or greater than about 90% in water.

Once the appropriate monomers in the appropriate amounts are selected, the polymeric microcarrier may be formed via polymerization reaction. In addition to the monomers that form the microcarrier, a composition for forming the microcarrier may include one or more additional compounds such as surfactants, wetting agents, photoinitiators, thermal initiators, catalysts, and activators.

Any suitable polymerization initiator may be employed. One of skill in the art will readily be able to select a suitable initiator, e.g. a radical initiator or a cationic initiator, suitable for use with the monomers. In various embodiments, UV light is used to generate free radical monomers to initiate chain polymerization. Examples of polymerization initiators include organic peroxides, azo compounds, quinones, nitroso compounds, acyl halides, hydrazones, mercapto compounds, pyrylium compounds, imidazoles, chlorotriazines, benzoin, benzoin alkyl ethers, diketones, phenones, or mixtures thereof. Examples of suitable commercially available, ultraviolet-activated and visible light-activated photoinitiators have tradenames such as IRGACURE 651, IRGACURE 184, IRGACURE 369, IRGACURE 819, DAROCUR 4265 and DAROCUR 1173 commercially available from Ciba Specialty Chemicals, Tarrytown, N.Y. and LUCIRIN TPO and LUCIRIN TPO-L commercially available from BASF (Charlotte, N.C.)

A photosensitizer may also be included in a suitable initiator system. Representative photosensitizers have carbonyl groups or tertiary amino groups or mixtures thereof. Photosensitizers having a carbonyl groups include benzophenone, acetophenone, benzil, benzaldehyde, o-chlorobenzaldehyde, xanthone, thioxanthone, 9,10-anthraquinone, and other aromatic ketones. Photosensitizers having tertiary amines include methyldiethanolamine, ethyldiethanolamine, triethanolamine, phenylmethyl-ethanolamine, and dimethylaminoethylbenzoate. Commercially available photosensitizers include QUANTICURE ITX, QUANTICURE QTX, QUANTICURE PTX, QUANTICURE EPD from Biddle Sawyer Corp.

In general, the amount of photosensitizer or photoinitiator system may vary from about 0.01 to 10% by weight.

Examples of cationic initiators that may be employed include salts of onium cations, such as arylsulfonium salts, as well as organometallic salts such as ion arene systems.

Examples of free radical initiators that may be employed include azo-type initiators such as 2-2'-azobis(dimethyl-valeronitrile), azobis(isobutyronitrile), azobis(cyclohexane-nitrite), azobis(methyl-butyronitrile), and the like, peroxide initiators such as benzoyl peroxide, lauroyl peroxide, methyl ethyl ketone peroxide, isopropyl peroxy-carbonate, 2,5-dienethyl-2,5-bas(2-ethylhexanoyl-peroxy)hexane, di-tert-butyl peroxide, cumene hydroperoxide, dichlorobenzoyl peroxide, potassium persulfate, ammonium persulfate, sodium bisulfate, combination of potassium persulfate, sodium bisulfate and the like, and mixtures thereof. Of course, any other suitable free radical initiators may be employed. An effective quantity of an initiator is generally within the range of from about 0.1 percent to about 15 percent by weight of the reaction mixture, such as from 0.1 percent to about 10 percent by weight or from about 0.1 percent to about 8 percent by weight of the reaction mixture.

In various embodiments, one or more monomers are diluted with water prior to undergoing polymerization.

(Meth)acrylate monomers, (meth)acrylamide monomers, or other suitable monomers may be synthesized as known in the art or obtained from a commercial vendor, such as Polysciences, Inc., Sigma Aldrich, Inc., and Sartomer, Inc.

E. Water-in-Oil Emulsion Copolymerization

Microcarriers may be formed in any suitable manner. It will be understood that the size and shape of the resulting polymeric microcarriers will be affected by the reaction conditions employed. In numerous embodiments, water-in-oil copolymerization is employed to form spherical microcarriers. Using such a reaction scheme and system, hydrophilic monomers can be dissolved in water and added to an oil or hydrophobic solution or suspension. Any suitable hydrophobic liquid, such as octanol, toluene, alkane, such as heptane, hexane or higher alkane including decane, dodecane, hexadecane, heavy mineral oil, silicone oil, fluorinated solvent, or the like may be used. An emulsifier may be added to promote the formation of the water-in-oil emulsion. Water insoluble (oil soluble) emulsifiers are preferred such as those having HLB value (hydrophilic lipophilic balance) lower than 9. Examples of such emulsifiers are Sorbitan trioleate (SPAN 85) HLB=1.8, Sorbitan tristearate (SPAN 65) HLB=2.1, Sorbitan sesquioleate (ARLACEL® 83) HLB=3.7, Glyceryl monostearate, HLB=3.8, Sorbitan monooleate, (SPAN 80) HLB=4.3, Sorbitan monostearate, (SPAN 60) HLB=4.7, Sorbitan monopalmitate, (SPAN 40) HLB=6.7 Sorbitan monolaurate, (SPAN 20) HLB=8.6. Hydrophobically modified water soluble polymers or random copolymers or block or graft copolymer which are built of components of different polarity are further examples of suitable emulsifiers. One example of a hydrophobically modified water soluble polymer emulsifier is ethyl cellulose. Of course other such emulsifiers may be employed.

Regardless of how microcarriers are prepared, in embodiments, that microcarriers have a density slightly greater than the cell culture medium in which they are to be suspended to facilitate separation of the microcarriers from the surrounding medium. In various embodiments, the microcarriers have a density of about 1.01 to 1.10 grams per cubic centimeter. Microcarriers having such a density should be readily maintained in suspension in cell culture medium with gentle stirring. It is expected that the density of the microcarriers can be easily tuned by varying the water to monomer ratio.

Figure 10:
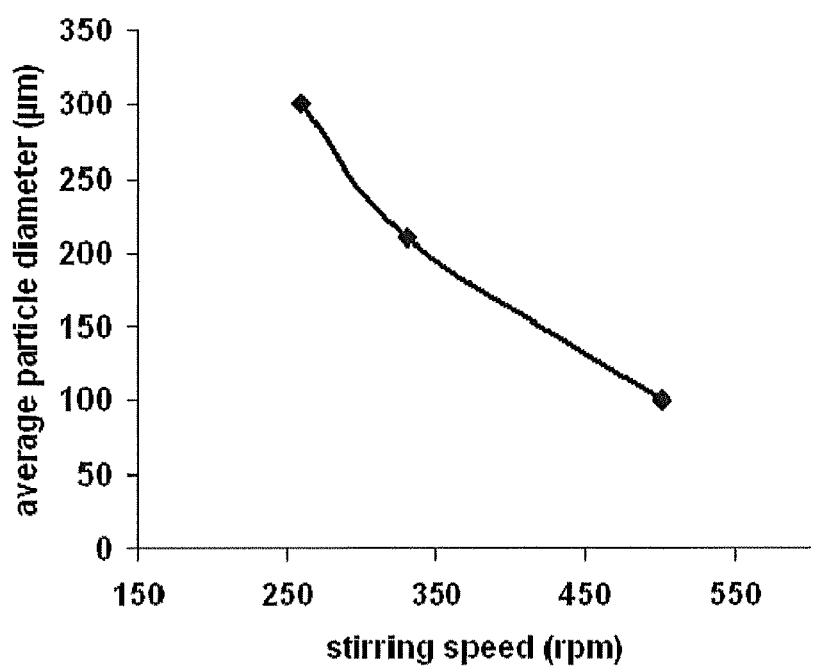
FIG. 10 is a graph showing the size of microcarriers obtained as a function of stirring rate.

In addition, it is preferred that the size variation of the microcarriers is sufficiently small to ensure that most, if not all, of the microcarriers can be suspended with gentle stirring. By way of example, the geometric size distribution of the microcarriers may be between about 1 and 1.4. Microcarriers may be of any suitable size. For example, microcarriers may have a diametric dimension of between about 20 microns and 1000 microns. Spherical microcarriers having such diameters can support the attachment of several hundred to thousands of cells per microcarrier. The size of the microcarriers formed via water-in-oil copolymerization techniques can be easily tuned by varying the stirring speed or the type of emulsifier used. For example, higher stirring speeds tend to result in smaller particle size (see, e.g., FIG. 10). In addition, it is believed that the use of polymeric emulsifiers, such as ethylcellulose, enables larger particles relative to lower molecular weight emulsifiers. Accordingly, one can readily modify stirring speed or agitation intensity and emulsifier to obtain microcarriers of a desired particle size.

It has been found that water-in-oil emulsion copolymerization can result in spherical microcarriers that are non-porous. As used herein, "non-porous" means having no pores or pores of an average size smaller than a cell with which the microcarrier is cultured, e.g., less than about 0.5-1 micrometers. Non-porous microspheres are desired when the microcarriers are not degradable, because cells that enter pores of macroporous microcarriers are difficult to remove. However, if the microcarriers are degradable, e.g. if they include an enzymatically or otherwise degradable cross-linker, it may be desirable for the microcarriers to be macroporous.

In some embodiments, microcarriers are optically transparent, allowing for easy microscopic observation of interaction of cells with a microcarrier. A transparent microcarrier allows for the observation of a cell on an opposing side (relative from the side from which it is viewed) of the microcarrier. The more transparent the microcarrier, the more readily the interaction can be observed via microscope. Microcarriers formed from 2-hydroxyethyl methacrylate, 2-carboxyethyl acrylate and dihydroxyethylene bisacrylamide were found to be highly transparent (see, e.g., Example 6 and FIG. 8). Microcarriers formed from other (i) uncharged hydrophilic unsaturated monomers having a hydroxyl group, (ii) hydrophilic carboxylic acid containing unsaturated monomers, and (iii) hydrophilic multifunctional unsaturated monomers should also be highly transparent, particularly when the monomers are (meth)acrylate or (meth)acrylamide monomers.

While not intending to be bound by theory, it is believed that more swellable microcarriers or microcarriers having high EWCs tend to form transparent microcarriers due to the high amount of water they absorb in culture media.

F. Conjugation of Polypeptide to Polymeric Microcarrier

Any suitable polypeptide may be conjugated to a microcarrier. Preferably, polypeptide includes an amino acid capable of conjugating to microcarrier; e.g. via the free carboxyl group formed from the hydrophyllic carboxylic acid containing unsaturated monomer. By way of example, any native or biomimetic amino acid having functionality that enables nucleophilic addition; e.g. via amide bond formation, may be included in polypeptide for purposes of conjugating to the microcarrier. Lysine, homolysine, ornithine, diaminoproprionic acid, and diaminobutanoic acid are examples of amino acids having suitable properties for conjugation to a carboxyl group of the microcarrier. In addition, the N-terminal alpha amine of a polypeptide may be used to conjugate to the carboxyl group, if the N-terminal amine is not capped. In various embodiments, the amino acid of polypeptide that conjugates with the microcarrier is at the carboxy terminal position or the amino terminal position of the polypeptide.

In numerous embodiments, the polypeptide, or a portion thereof, has cell adhesive activity; i.e., when the polypeptide is conjugated to the microcarrier, the polypeptide allows a cell to adhere to the surface of the peptide-containing microcarrier. By way of example, the polypeptide may include an amino sequence, or a cell adhesive portion thereof, recognized by proteins from the integrin family or leading to an interaction with cellular molecules able to sustain cell adhesion. For example, the polypeptide may include an amino acid sequence derived from collagen, keratin, gelatin, fibronectin, vitronectin, laminin, bone sialoprotein (BSP), or the like, or portions thereof. In various embodiments, polypeptide includes an amino acid sequence of ArgGlyAsp (RGD).

Microcarriers as described herein provide a synthetic surface to which any suitable adhesion polypeptide or combinations of polypeptides may be conjugated, providing an alternative to biological substrates or serum that have unknown components. In current cell culture practice, it is known that some cell types require the presence of a biological polypeptide or combination of peptides on the culture surface for the cells to adhere to the surface and be sustainably cultured. For example, HepG2/C3A hepatocyte cells can attach to plastic culture ware in the presence of serum. It is also known that serum can provide polypeptides that can adhere to plastic culture ware to provide a surface to which certain cells can attach. However, biologically-derived substrates and serum contain unknown components. For cells where the particular component or combination of components (peptides) of serum or biologically-derived substrates that cause cell attachment are known, those known polypeptides can be synthesized and applied to a microcarrier as described herein to allow the cells to be cultured on a synthetic surface having no or very few components of unknown origin or composition.

For any of the polypeptides discussed herein, it will be understood that a conservative amino acid may be substituted for a specifically identified or known amino acid. A "conservative amino acid", as used herein, refers to an amino acid that is functionally similar to a second amino acid. Such amino acids may be substituted for each other in a polypeptide with a minimal disturbance to the structure or function of the polypeptide according to well known techniques. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q).

A linker or spacer, such as a repeating poly(ethylene glycol) linker or any other suitable linker, may be used to increase distance from polypeptide to surface of microcarrier. The linker may be of any suitable length. For example, if the linker is a repeating poly(ethylene glycol) linker, the linker may contain between 2 and 10 repeating ethylene glycol units. In some embodiments, the linker is a repeating poly (ethylene glycol) linker having about 4 repeating ethylene glycol units. All, some, or none of the polypeptides may be conjugated to a microcarrier via linkers. Other potential linkers that may be employed include polypeptide linkers such as poly(glycine) or poly(β-alanine).

A polypeptide may be conjugated to the microcarrier at any density, preferably at a density suitable to support culture of undifferentiated stem cells or other cell types. For example, polypeptides may be conjugated to a microcarrier at a density of between about 1 pmol per mm$^2$ and about 50 pmol per mm$^2$ of surface of the microcarrier. For example, the polypeptide may be present at a density of greater than 5 pmol/mm$^2$, greater than 6 pmol/mm$^2$, greater than 7 pmol/mm$^2$, greater than 8 pmol/mm$^2$, greater than 9 pmol/mm$^2$, greater than 10 pmol/mm$^2$, greater than 12 pmol/mm$^2$, greater than 15 pmol/mm$^2$, or greater than 20 pmol/mm$^2$ of the surface of the microcarrier. It will be understood that the amount of polypeptide present can vary depending on the composition of the microcarrier, the size of the microcarrier, the nature of the polypeptide itself, and the type of cell to be cultured.

While not intending to be bound by theory, it is believed that stem cells, including embryonic stem cells, may require higher peptide densities to support cell attachment than some other types of cells, such as, for example, HT1080 cells (see, e.g., EXAMPLE 17). In addition, cells may require higher peptide density to sufficiently attach to microcarriers under stirred conditions relative to static conditions. In various embodiments, microcarriers have greater than 50 nmol conjugated polypeptide per milligram of microcarrier base. For example, a microcarrier may have greater than 60, greater than 70, greater than 80, greater than 90, or greater than 100 nmol conjugated polypeptide per milligram of microcarrier base. In some embodiments where the microcarriers are intended to be used for culturing stem cells, the microcarriers have greater than 100 nmol conjugated polypeptide per milligram of microcarrier base.

A polypeptide may be conjugated to the polymerized microcarrier via any suitable technique. A polypeptide may be conjugated to a polymerized microcarrier via an amino terminal amino acid, a carboxy terminal amino acid, or an internal amino acid. One suitable technique involves 1-ethyl-3-[3-dimethylaminopropyl]carbodiimide hydrochloride (EDC)/N-hydroxysuccinimide (NHS) chemistry, as generally known in the art. EDC and NHS or N-hydroxysulfosuccinimide (sulfo-NHS) can react with carboxyl groups of the swellable (meth)acrylate layer to produce amine reactive NHS esters. EDC reacts with a carboxyl group of the swellable (meth)acrylate layer to produce an amine-reactive O-acylisourea intermediate that is susceptible to hydrolysis. The addition of NHS or sulfo-NHS stabilizes the amine-reactive O-acylisourea intermediate by converting it to an amine reactive NHS or sulfo-NHS ester, allowing for a two step procedure. Following activation of the swellable (meth) acrylate layer, the polypeptide may then be added and the terminal amine of the polypeptide can react with the amine reactive ester to form a stable amide bond, thus conjugating the polypeptide to the swellable (meth)acrylate layer. When EDC/NHS chemistry is employed to conjugate a polypeptide to the swellable (meth)acrylate layer, the N-terminal amino acid is preferably an amine containing amino acid such as lysine, ornithine, diaminobutyric acid, or diaminoproprionic acid. Of course, any acceptable nucleophile may be employed, such as hydroxylamines, hydrazines, hydroxyls, and the like.

EDC/NHS chemistry results in a zero length crosslinking of polypeptide to microcarrier. Linkers or spacers, such as poly(ethylene glycol) linkers (e.g., available from Quanta BioDesign, Ltd.) with a terminal amine may be added to the N-terminal amino acid of polypeptide. When adding a linker to the N-terminal amino acid, the linker is preferably a N-PG-amido-PEG$_X$-acid where PG is a protecting group such as the Fmoc group, the BOC group, the CBZ group or any other group amenable to peptide synthesis and X is 2, 4, 6, 8, 12, 24 or any other discrete PEG which may be available.

In various embodiments, a 1 μM-10.000 μM polypeptide fluid composition, such as a solution, suspension, or the like, is contacted with activated microcarriers to conjugate the polypeptide. For example the polypeptide concentration may be between about 100 μM and about 2000 μM, between about 500 μM and about 1500 μM, or about 1000 μM. It will be understood that the volume of the polypeptide composition and the concentration may be varied to achieve a desired density of polypeptide conjugated to the microcarrier.

The polypeptide may be cyclized or include a cyclic portion. Any suitable method for forming cyclic polypeptide may be employed. For example, an amide linkage may be created by cyclizing the free amino functionality on an appropriate amino-acid side chain and a free carboxyl group of an appropriate amino acid side chain. Also, a di-sulfide linkage may be created between free sulfhydryl groups of side chains appropriate amino acids in the peptide sequence. Any suitable technique may be employed to form cyclic polypeptides (or portions thereof). By way of example, methods described in, e.g., WO1989005150 may be employed to form cyclic polypeptides. Head-to-tail cyclic polypeptides, where the polypeptides have an amide bond between the carboxy terminus and the amino terminus may be employed. An alternative to the disulfide bond would be a diselenide bond using two selenocysteines or mixed selenide/sulfide bond, e.g., as described in Koide et al, 1993, Chem. Pharm. Bull. 41(3): 502-6; Koide et al., 1993, Chem. Pharm. Bull. 41(9):1596-1600; or Besse and Moroder, 1997, Journal of Peptide Science, vol. 3, 442-453.

Polypeptides may be synthesized as known in the art (or alternatively produced through molecular biological techniques) or obtained from a commercial vendor, such as American Peptide Company, CEM Corporation, or GenScript Corporation. Linkers may be synthesized as known in the art or obtained from a commercial vendor, such as discrete polyethylene glycol (dPEG) linkers available from Quanta BioDesign, Ltd.

An example of a polypolypeptide that may be conjugated to a microcarrier is a polypeptide that includes KGGNGEPRGDTYRAY (SEQ ID NO:1), which is an RGD-containing sequence from bone sialoprotein with an additional "KGG" sequence added to the N-terminus. The lysine (K) serves as a suitable nucleophile for chemical conjugation, and the two glycine amino acids (GG) serve as spacers. Cystine (C), or another suitable amino acid, may alternatively be used for chemical conjugation, depending on the conjugation method employed. Of course, a conjugation or spacer sequence (KGG or CGG, for example) may be present or absent. Additional examples of suitable polypeptides for conjugation with microcarriers (with or without conjugation or spacer sequences) are polypeptides that include NGEPRGDTYRAY, (SEQ ID NO:2), GRGDSPK (SEQ ID NO:3) (short fibronectin) AVTGRGDSPASS (SEQ ID NO:4) (long FN), PQVTRGDVFTMP (SEQ ID NO:5) (vitronectin), RNIAEIIKDI (SEQ ID NO:6) (lamininβ1), KYGRKRLQVQLSIRT (SEQ ID NO:7) (mLMα1 res 2719-2730), NGEPRGDTRAY (SEQ ID NO:8) (BSP-Y), NGEPRGDTYRAY (SEQ ID NO:9) (BSP), KYGAASIKVAVSADR (SEQ ID NO:10) (mLMα1 res 2122-2132), KYGKAFDITYVRLKF (SEQ ID NO:11) (mLMγ1 res 139-150), KYGSETTVKYIFRLHE (SEQ ID NO:12) (mLMγ1 res 615-627), KYGTDIRVTLN-RLNTF (SEQ ID NO:13) (mLMγ1 res 245-257), TSIKIRG-TYSER (SEQ ID NO:14) (mLMγ1 res 650-261), TWYKI-AFQRNRK (SEQ ID NO:15) (mLMα1 res 2370-2381), SINNNRWHSIYITRFGNMGS (SEQ ID NO:16) (mLMα1 res 2179-2198), KYGLALERKDHSG (SEQ ID NO:17) (tsp1 RES 87-96), or GQKCIVQTTSWSQCSKS (SEQ ID NO:18) (Cyr61 res 224-240).

In some embodiments, the peptide comprises KGGK$^4$DGEPRGDTYRATD$^{17}$ (SEQ ID NO:19), where Lys$^4$ and Asp$^{17}$ together form an amide bond to cyclize a portion of the polypeptide; KGGL$^4$EPRGDTYRD$^{13}$ (SEQ ID NO:20), where Lys$^4$ and Asp$^{13}$ together form an amide bond to cyclize a portion of the polypeptide; KGGC$^4$NGEPRGDTYRATC$^{17}$ (SEQ ID NO:21), where Cys$^4$ and Cys$^{17}$ together form a disulfide bond to cyclize a portion of the polypeptide; KGGC$^4$EPRGDTYRC$^{13}$ (SEQ ID NO:22), where Cys$^4$ and Cys$^{13}$ together form a disulfide bond to cyclize a portion of the polypeptide, or KGGAVT-GDGNSPASS (SEQ ID NO:23).

In embodiments, the polypeptide may be acetylated or amidated or both. While these examples are provided, those of skill in the art will recognize that any peptide or polypeptide sequence may be conjugated to a microcarrier as described herein.

2. Cell Culture Articles

Microcarriers as described herein may be used in any suitable cell culture system. Typically microcarriers and cell culture media are placed in a suitable cell culture article and the microcarriers are stirred or mixed in the media. Suitable cell culture articles include bioreactors, such as the WAVE BIOREACTOR® (Invitrogen), single and multi-well plates, such as 6, 12, 96, 384, and 1536 well plates, jars, petri dishes, flasks, multi-layered flasks, beakers, plates, roller bottles, tubes, bags, membranes, cups, spinner bottles, perfusion chambers, bioreactors, CellSTACK® culture chambers (Corning Incorporated) and fermenters.

3. Incubating Cells in Culture Media Having Microcarriers Containing Conjugated Polypeptide A cell culture article housing culture media containing conjugated polypeptide as described above may be seeded with cells. The conjugated polypeptide employed may be selected based on the type of cell being cultured. The cells may be of any cell type. For example, the cells may be connective tissue cells, epithelial cells, endothelial cells, hepatocytes, skeletal or smooth muscle cells, heart muscle cells, intestinal cells, kidney cells, or cells from other organs, stem cells, islet cells, blood vessel cells, lymphocytes, cancer cells, primary cells, cell lines, or the like. The cells may be mammalian cells, preferably human cells, but may also be non-mammalian cells such as bacterial, yeast, or plant cells.

In numerous embodiments, the cells are stem cells which, as generally understood in the art, refer to cells that have the ability to continuously divide (self-renewal) and that are capable of differentiating into a diverse range of specialized cells. In some embodiments, the stem cells are multipotent, totipotent, or pluripotent stem cells that may be isolated from an organ or tissue of a subject. Such cells are capable of giving rise to a fully differentiated or mature cell types. A stem cell may be a bone marrow-derived stem cell, autologous or otherwise, a neuronal stem cell, or an embryonic stem cell. A stem cell may be nestin positive. A stem cell may be a hematopoietic stem cell. A stem cell may be a multi-lineage cell derived from epithelial and adipose tissues, umbilical cord blood, liver, brain or other organ. In various embodiments, the stem cells are pluripotent stem cells, such as pluripotent embryonic stem cells isolated from a mammal. Suitable mammals may include rodents such as mice or rats, primates including human and non-human primates. In various embodiments, the microcarrier with conjugated polypeptide supports undifferentiated culture of embryonic stem cells for 5 or more passages, 7 or more passages, or 10 or more passages. Typically stems cells are passaged to a new surface after they reach about 75% confluency. The time for cells to reach 75% confluency is dependent on media, seeding density and other factors as know to those in the art.

Because human embryonic stem cells (hESC) have the ability to grown continually in culture in an undifferentiated state, the hESC for use with microcarriers as described herein may be obtained from an established cell line. Examples of human embryonic stem cell lines that have been established include, but are not limited to, H1, H7, H9, H13 or H14 (available from WiCell established by the University of Wisconsin) (Thompson (1998) Science 282:1145); hESBGN-01, hESBGN-02, hESBGN-03 (BresaGen, Inc., Athens, Ga.); HES-1, HES-2, HES-3, HES-4, HES-5, HES-6 (from ES Cell International, Inc., Singapore); HSF-1, HSF-6 (from University of California at San Francisco); I 3, I 3.2, I 3.3, I 4, I 6, I 6.2, J 3, J 3.2 (derived at the Technion-Israel Institute of Technology, Haifa, Israel); UCSF-1 and UCSF-2 (Genbacev et al., Fertil. Steril. 83(5):1517-29, 2005); lines HUES 1-17 (Cowan et al., NEJM 350(13):1353-56, 2004); and line ACT-14 (Klimanskaya et al., Lancet, 365(9471):1636-41, 2005). Embryonic stem cells may also be obtained directly from primary embryonic tissue. Typically this is done using frozen in vitro fertilized eggs at the blastocyst stage, which would otherwise be discarded.

Other sources of pluripotent stem cells include induced primate pluripotent stem (iPS) cells. iPS cells refer to cells, obtained from a juvenile or adult mammal, such as a human, that are genetically modified, e.g., by transfection with one or more appropriate vectors, such that they are reprogrammed to attain the phenotype of a pluripotent stem cell such as an hESC. Phenotypic traits attained by these reprogrammed cells include morphology resembling stem cells isolated from a blastocyst as well as surface antigen expression, gene expression and telomerase activity resembling blastocyst derived embryonic stem cells. The iPS cells typically have the ability to differentiate into at least one cell type from each of the primary germ layers: ectoderm, endoderm and mesoderm. The iPS cells, like hESC, also form teratomas when injected into immuno-deficient mice, e.g., SCID mice. (Takahashi et al., (2007) Cell 131(5):861; Yu et al., (2007) Science 318: 5858).

To maintain stem cells in an undifferentiated state it may be desirable to minimize non-specific interaction or attachment of the cells with the surface of the microcarrier, while obtaining selective attachment to the polypeptide(s) attached to the surface. The ability of stem cells to attach to the surface of a microcarrier without conjugated polypeptide may be tested prior to conjugating polypeptide to determine whether the microcarrier provides for little to no non-specific interaction or attachment of stem cells. Once a suitable microcarrier has been selected, cells may be seeded in culture medium containing the microcarriers.

Prior to seeding, the cells, regardless of cell type, may be harvested and suspended in a suitable medium, such as a growth medium in which the cells are to be cultured once seeded. For example, the cells may be suspended in and cultured in a serum-containing medium, a conditioned medium, or a chemically-defined medium. As used herein, "chemically-defined medium" means cell culture media that contains no components of unknown composition. Chemically defined cell culture media may, in various embodiments, contain no proteins, hydrosylates, or peptides of unknown composition. In some embodiments, chemically defined media contains polypeptides or proteins of known composition, such as recombinant growth hormones. Because all components of chemically-defined media have a known chemical structure, variability in culture conditions and thus variability in cell response can be reduced, increasing reproducibility. In addition, the possibility of contamination is reduced. Further, the ability to scale up is made easier due, at least in part, to the factors discussed above. Chemically defined cell culture media are commercially available from Invitrogen (Invitrogen Corporation, 1600 Faraday Avenue, PO Box 6482, Carlsbad, Calif. 92008) as STEM PRO, a fully serum- and feeder-free (SFM) specially formulated from the growth and expansion of embryonic stem cells, Xvivo (Lonza), and Stem Cell Technologies, Inc. as mTeSR™1 maintenance media for human embryonic stem cells.

One or more growth or other factors may be added to the medium in which cells are incubated with the microcarriers conjugated to polypeptide. The factors may facilitate cellular proliferation, adhesion, self-renewal, differentiation, or the like. Examples of factors that may be added to or included in the medium include muscle morphogenic factor (MMP), vascular endothelium growth factor (VEGF), interleukins, nerve growth factor (NGF), erythropoietin, platelet derived growth factor (PDGF), epidermal growth factor (EGF), activin A (ACT) such as activin A, hematopoietic growth factors, retinoic acid (RA), interferons, fibroblastic growth factors, such as basic fibroblast growth factor (bFGF), bone morphogenetic protein (BMP), peptide growth factors, heparin binding growth factor (HBGF), hepatocyte growth factor, tumor necrosis factors, insulin-like growth factors (IGF) I and II, transforming growth factors, such as transforming growth factor-β1 (TGFβ1), and colony stimulating factors.

The cells may be seeded at any suitable concentration. Typically, the cells are seeded at about 10,000 cells/cm$^2$ of microcarrier to about 500,000 cells/cm$^2$. For example, cells may be seeded at about 50,000 cells/cm$^2$ of substrate to about 150,000 cells/cm$^2$. However, higher and lower concentrations may readily be used. The incubation time and conditions, such as temperature, $CO_2$ and $O_2$ levels, growth medium, and the like, will depend on the nature of the cells being cultured and can be readily modified. The amount of time that the cells are cultured with the microcarriers may vary depending on the cell response desired.

The cultured cells may be used for any suitable purpose, including (i) obtaining sufficient amounts of undifferentiated stem cells cultured on a synthetic surface in a chemically defined medium for use in investigational studies or for developing therapeutic uses, (ii) for investigational studies of the cells in culture, (iii) for developing therapeutic uses, (iv) for therapeutic purposes, (v) for studying gene expression, e.g. by creating cDNA libraries, (vi) for studying drug and toxicity screening, and (vii) the like.

One suitable way to determine whether cells are undifferentiated is to determine the presence of the OCT4 marker. In various embodiments, the undifferentiated stems cells cultured on microcarriers as described herein for 5, 7, or 10 or more passages retain the ability to be differentiated.

4. Synopsis

The microcarriers described herein have microcarrier bases formed from monomers comprising (i) an uncharged hydrophilic unsaturated monomer having a hydroxyl group, (ii) a hydrophilic carboxylic acid containing unsaturated monomer, and (iii) a hydrophilic multifunctional unsaturated monomer. Any suitable monomers may be used. In various embodiments, the monomers are hydrophilic (meth)acrylate monomers or hydrophilic (meth)acrylamide monomers.

For example, the uncharged hydrophilic unsaturated monomer having a hydroxyl group may be a monomer having Formula I or Formula II as described above. Examples of suitable uncharged hydrophilic unsaturated monomers that may be employed include hydroxypropyl methacrylate, 2-hydroxyethyl methacrylate, 2-hydroxyethyl acrylate, glycerol methacrylate, hydroxypropyl acrylate, 4-hydroxybutyl acrylate, N-(hydroxymethyl)acrylamide, N-[Tris(hydroxymethyl)methyl]acrylamide, 3-acryloylamino-1-propanol, N-acrylamido-ethoxyethanol, and N-hydroxyethyl acrylamide.

The hydrophilic carboxylic acid containing unsaturated monomer may be monomers according to Formula III or IV described above. Specific examples include 2-carboxyethyl methacrylate, 2-carboxyethyl acrylate, acrylic acid, methacrylic acid, 2-carboxyethyl acrylamide, and acrylamidoglycolic acid.

Examples of suitable hydrophilic multifunctional unsaturated monomer include di-, tri- or higher functional (meth)acrylate or (meth)acrylamide monomers such as N,N'methylenebisacrylamide, N,N'(1,2dihydroxyethylene) bisacrylamide, polyethylene glycol di(meth)acrylate, triglycerol diacrylate, propylene glycol glycerolate diacrylate, trimethylolpropane ethoxylate triacrylate, glycerol 1,3-diglycerolate diacrylate. As described above, it may be desirable to include a hydrophobic crosslinking monomer, which may be any suitable hydrophobic crosslinking monomer, such as a di-, tri-, or higher functional (meth)acrylate or (meth)acrylamide monomers. An example of hydrophobic cross-linking monomers that may be employed is tetra(ethylene glycol) dimethacrylate. In various embodiments, the hydrophilic multifunctional unsaturated monomer is more hydrophilic than tetra(ethylene glycol) dimethacrylate or tetra(ethylene glycol) diacrylate.

The microcarrier base may be formed from any suitable mixture of the monomers discussed above. In various embodiments, the mixture of monomers used to form the microcarrier includes (i) about 30 to about 70 parts per weight of the uncharged hydrophilic unsaturated monomer having a hydroxyl group; (ii) about 20 to about 60 parts per weight of the hydrophilic carboxylic acid containing unsaturated monomer; and (iii) 1 to 15 parts by weight of the hydrophilic multifunctional unsaturated monomer. A hydrophilic multifunctional unsaturated monomer (e.g., methylene bisacrylamide or dihydroxyethylene bisacrylamide) may be used in combination with a less hydrophilic or hydrophobic unsaturated monomer (e.g., tetra(ethylene glycol) dimethacrylate). In many of such embodiments, the total crosslinker (multifunctional unsaturated monomer) does not exceed 15 parts by weight of the mixture of monomers, with the more hydrophilic multifunctional unsaturated monomer being at least 1% by weight of the mixture of monomers.

Various embodiments of the microcarrier bases have an EWC of greater than about 70%, greater than about 75%, greater than about 80%, greater than about 85%, or greater than about 90% in water.

In various embodiments, the pendant carboxyl content (from the hydrophilic carboxylic acid containing unsaturated monomer) of the polymeric microcarrier is greater than 1, greater than 2, greater than 3, or about 4 milliequivalents per gram.

The present disclosure described and contemplates, compositions comprising the various monomers for forming the microcarriers. For example, a composition for forming a microcarrier (whether via water-in-oil emulsion copolymerization or other method) may include (i) an uncharged hydrophilic unsaturated monomer having a hydroxyl group, (ii) a hydrophilic carboxylic acid containing unsaturated monomer, and (iii) a hydrophilic multifunctional unsaturated monomer, such as those described above. The monomers may be present in the composition is any suitable ratio, such as those described above with regard to the microcarrier bases.

The microcarrier base may be prepared according to any suitable process. In various embodiments, water-in-oil emulsion copolymerization is used to form the microcarrier base. Using such a reaction scheme and system, hydrophilic monomers can be dissolved in water and added to an oil or hydrophobic solution or suspension. Any suitable hydrophobic liquid, such as octanol, toluene, alkane, such as heptane, hexane or higher alkane including decane, dodecane, hexadecane, heavy mineral oil, silicone oil, fluorinated solvent, or the like may be used. An emulsifier may be added to promote the formation of the water-in-oil emulsion. Water insoluble (oil soluble) emulsifiers are preferred such as those having HLB value (hydrophilic lipophilic balance) lower than 9. Examples of such emulsifiers are Sorbitan trioleate (SPAN 85) HLB=1.8, Sorbitan tristearate (SPAN 65) HLB=2.1, Sorbitan sesquioleate (ARLACEL® 83) HLB=3.7, Glyceryl monostearate, HLB=3.8, Sorbitan monooleate, (SPAN 80) HLB=4.3, Sorbitan monostearate, (SPAN 60) HLB=4.7, Sorbitan monopalmitate, (SPAN 40) HLB=6.7 Sorbitan monolaurate, (SPAN 20) HLB=8.6. Hydrophobically modified water soluble polymers or random copolymers or block or graft copolymer which are built of components of different polarity are further examples of suitable emulsifiers. One example of a hydrophobically modified water soluble polymers emulsifier is ethyl cellulose. Of course other such emulsifiers may be employed.

The microcarriers described herein may also include a polypeptide conjugated to the microcarrier base. Any suitable process may be employed to conjugate the polypeptide. In various embodiments, the polypeptide is conjugated to a carboxylic acid group resulting from the hydrophilic carboxylic acid containing unsaturated monomer. EDC/NHS or any other suitable chemistry may be used to conjugate the polypeptide to a carboxylic acid group of the microcarrier base. A microcarrier may have greater than 60, greater than 70, greater than 80, greater than 90, or greater than 100 nmol conjugated polypeptide per milligram of microcarrier base. In some embodiments where the microcarriers are intended to be used for culturing stein cells, the microcarriers have greater than 100 nmol conjugated polypeptide per milligram of microcarrier base.

Any suitable polypeptide may be conjugated to the microcarrier base. Preferably, the polypeptide facilitates cell adhesion to the microcarrier in a bio-specific manner. In various embodiments, the polypeptide includes an amino acid sequence, or portion thereof, recognized by proteins from the integrin family or leading to an interaction with cellular molecules able to sustain cell adhesion. For example, the polypeptide may include an amino acid sequence derived from collagen, keratin, gelatin, fibronectin, vitronectin, laminin, bone sialoprotein (BSP), or the like, or portions thereof. In various embodiments, polypeptide includes an amino acid sequence of ArgGlyAsp (RGD).

Examples of polypeptides that may be conjugated to a microcarrier base include KGGNGEPRGDTYRAY (SEQ ID NO:1); NGEPRGDTYRAY, (SEQ ID NO:2); GRGDSPK (SEQ ID NO:3); AVTGRGDSPASS (SEQ ID NO:4); PQVTRGDVFTMP (SEQ ID NO:5); RNIAEIIKDI (SEQ ID NO:6); KYGRKRLQVQLSIRT (SEQ ID NO:7); NGEPRGDTRAY (SEQ ID NO:8); NGEPRGDTYRAY (SEQ ID NO:9); KYGAASIKVAVSADR (SEQ ID NO:10); KYGKAFDITYVRLKF (SEQ ID NO:11); KYGSETTVKYIFRLHE (SEQ ID NO:12); KYGTDIRVTLNRLNTF (SEQ ID NO:13); TSIKIRGTYSER (SEQ ID NO:14); TWYKIAFQRNRK (SEQ ID NO:15); SINNNRWHSIYITRFGNMGS (SEQ ID NO:16); KYGLALERKDHSG (SEQ ID NO:17); GQKCIVQTTSWSQCSKS (SEQ ID NO:18); KGGK$^4$DGEPRGDTYRATD$^{17}$ (SEQ ID NO:19), where Lys$^4$ and Asp$^{17}$ together form an amide bond to cyclize a portion of the polypeptide; KGGL$^4$EPRGDTYRD$^{13}$ (SEQ ID NO:20), where Lys$^4$ and Asp$^{13}$ together form an amide bond to cyclize a portion of the polypeptide; KGGC$^4$NGEPRGDTYRATC$^{17}$ (SEQ ID NO:21), where Cys$^4$ and Cys$^{17}$ together form a disulfide bond to cyclize a portion of the polypeptide; KGGC$^4$EPRGDTYRC$^{13}$ (SEQ ID NO:22), where Cys$^4$ and Cys$^{13}$ together form a disulfide bond to cyclize a portion of the polypeptide, KGGAVTGDGNSPASS (SEQ ID NO:23); and Ac-Lys-Gly-Gly-Pro-Gln-Val-Thr-Arg-Gly-Asp-Val-Phe-Thr-Met-Pro-NH$_2$ (SEQ ID NO:24).

A polypeptide may be conjugated to the microcarrier at any density, preferably at a density suitable to support culture of undifferentiated stein cells or other cell types. Polypeptides may be conjugated to a microcarrier at a density of between about 1 pmol per mm$^2$ and about 50 pmol per mm$^2$ of surface of the microcarrier. For example, the polypeptide may be present at a density of greater than 5 pmol/mm$^2$, greater than 6 pmol/mm$^2$, greater than 7 pmol/mm$^2$, greater than 8 pmol/mm$^2$, greater than 9 pmol/mm$^2$, greater than 10 pmol/mm$^2$, greater than 12 pmol/mm$^2$, greater than 15 pmol/mm$^2$, or greater than 20 pmol/mm$^2$ of the surface of the microcarrier.

The microcarriers described herein may be employed in any suitable system. Such as bio-reactors, single and multi-well plates, jars, petri dishes, flasks, beakers, roller bottles, tubes, bags, membranes, cups, spinner bottles, perfusion chambers, fermenters, and the like.

The microcarriers, in an appropriate system, may be used to culture any suitable cells, such as mammalian cells, preferably human cells, or non-mammalian cells such as bacterial, yeast, or plant cell. Examples of mammalian cells that may be cultured with the microcarriers described herein include connective tissue cells, epithelial cells, endothelial cells, hepatocytes, skeletal or smooth muscle cells, heart muscle cells, intestinal cells, kidney cells, or cells from other organs, stem cells, islet cells, blood vessel cells, lymphocytes, cancer cells, primary cells, cell lines, or the like. In numerous embodiments, the cells are stem cells which, as such as multipotent, totipotent, or pluripotent stem cells. In some embodiments the cells are embryonic stem cells. As shown herein, the described microcarriers may be used to culture embryonic stem cells in chemically-defined medium.

The cultured cells may be used for any suitable purpose, including (i) obtaining sufficient amounts of undifferentiated stem cells cultured on a synthetic surface in a chemically defined medium for use in investigational studies or for developing therapeutic uses, (ii) for investigational studies of the cells in culture, (iii) for developing therapeutic uses, (iv) for therapeutic purposes, (v) for studying gene expression, e.g. by creating cDNA libraries, (vi) for studying drug and toxicity screening, and (vii) the like.

In a first aspect, a microcarrier for cell culture, comprising: a polymeric microcarrier base formed from copolymerization of a mixture of monomers including (i) an uncharged hydrophilic unsaturated monomer having a hydroxyl group selected from a hydrophilic (meth)acrylate monomer having a hydroxyl group or a hydrophilic (meth)acrylamide monomer having a hydroxyl group, (ii) a hydrophilic carboxylic acid containing unsaturated monomer selected from a carboxylic acid containing (meth)acrylate monomer or a carboxylic acid containing (meth)acrylamide monomer, and (iii) a first hydrophilic multifunctional unsaturated monomer selected from a hydrophilic multifunctional (meth)acrylate monomer or a hydrophilic multifunctional (meth)acrylamide monomer; and a polypeptide conjugated to the microcarrier base, wherein the microcarrier base has an equilibrium water content of greater than 75% is provided. In a second aspect, a microcarrier according to aspect 1, wherein the mixture of monomers includes (i) 30 to 70 parts per weight of the uncharged hydrophilic unsaturated monomer having a hydroxyl group; (ii) 20 to 60 parts per weight of the hydrophilic carboxylic acid containing unsaturated monomer; and (iii) 1 to 15 parts by weight of the first hydrophilic multifunctional unsaturated monomer is provided. In a third aspect, a microcarrier according to aspect 1 or 2, wherein the uncharged hydrophilic unsaturated monomer having a hydroxyl group is a monomer according to Formula (I) or Formula (II):

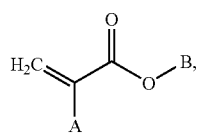

(I)

where A is H or methyl, and where B is C1-C6 straight or branched chain alcohol or ether. In some embodiments, B is C1-C4 straight or branched chain alcohol; or

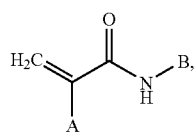

(II)

where A is hydrogen or methyl, and where B is C1-C6 straight or branched chain alcohol or ether is provided. In a fourth aspect, a microcarrier according to aspect 1 or 2, wherein the uncharged hydrophilic unsaturated monomer having a hydroxyl group is selected from the group consisting of hydroxypropyl methacrylate, 2-hydroxyethyl methacrylate, 2-hydroxyethyl acrylate, glycerol methacrylate, hydroxypropyl acrylate, 4-hydroxybutyl acrylate, N-(hydroxymethyl)acrylamide, N-[Tris(hydroxymethyl)methyl]acrylamide, 3-acryloylamino-1-propanol, N-acrylamido-ethoxyethanol, and N-hydroxyethyl acrylamide is provided. In a fifth aspect, a microcarrier according to aspect 1 or 2, wherein the uncharged hydrophilic unsaturated monomer having a hydroxyl group is 2-hydroxyethyl methacrylate is provided. In a sixth aspect, a microcarrier according to any of aspects 1-5, wherein the hydrophilic carboxylic acid containing unsaturated monomer is a monomer according to Formula (III) or Formula (IV):

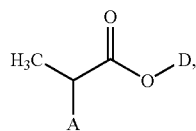

(III)

where A is hydrogen or methyl, and where D is C1-C6 straight or branched chain alkyl substituted with a carboxyl group (—COOH); or

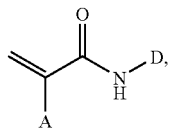

(IV)

where A is hydrogen or methyl, and where D is C1-C6 straight or branched chain alkyl substituted with a carboxyl group (—COOH). In a seventh aspect, microcarrier according to any of aspects 1-5, wherein the hydrophilic carboxylic acid containing unsaturated monomer is selected from the group consisting of 2-carboxyethyl methacrylate, 2-carboxyethyl acrylate, acrylic acid, methacrylic acid, 2-carboxyethyl acrylamide, and acrylamidoglycolic acid is provided. In an eighth aspect, a microcarrier according to any of aspects 1-5, wherein the hydrophilic carboxylic acid containing unsaturated monomer is 2-carboxyethyl methacrylate. In a ninth aspect, microcarrier according to any of aspects 1-8, wherein the first hydrophilic multifunctional unsaturated monomer is selected from the group consisting of N,N'methylenebisacrylamide, N,N'(1,2-dihydroxyethylene)bisacrylamide, polyethylene glycol di(meth)acrylate, triglycerol diacrylate, propylene glycol glycerolate diacrylate, trimethylolpropane ethoxylate triacrylate, and glycerol 1,3-diglycerolate diacrylate is provided. In a tenth aspect, a microcarrier according to any of aspects 1-8, wherein the first hydrophilic multifunctional unsaturated monomer is selected from the group consisting of methylene bisacrylamide and dihydroxyethylene bisacrylamide is provided. In an eleventh aspect a microcarrier according to any of aspects 1-10, wherein the mixture of monomers further comprises a second multifunctional unsaturated monomer selected from a multifunctional unsaturated (meth)acrylate monomer or a multifunctional unsaturated (meth)acrylamide monomer is provided. In a twelfth aspect, a microcarrier according to aspect 11, wherein the second multifunctional unsaturated monomer is less hydrophilic than the first hydrophilic multifunctional unsaturated monomer is provided. In a thirteenth aspect, a microcarrier according to aspect 11 or claim 12, wherein the second multifunctional unsaturated monomer is tetra(ethylene glycol) dimethacrylate is provided. In a fourteenth aspect, a microcarrier according to any of aspects 11-13, wherein the first hydrophilic multifunctional unsaturated monomer and the second multifunctional unsaturated monomer together do not exceed 15 parts by weight of the mixture of monomers. In a fifteenth aspect, a microcarrier according to any of aspects 1-14, wherein the polypeptide is an RGD-containing polypeptide is provided. In a sixteenth aspect, a microcarrier according to any of aspects 1-14, wherein the polypeptide is selected from the group consisting of a BSP polypeptide, a vitronectin polypeptide, a fibronectin polypeptide, and a collagen polypeptide is provided. In a seventeenth aspect, a microcarrier according to any of aspects 1-16, wherein the microcarrier has greater than 100 nmol conjugated polypeptide per milligram of microcarrier base is provided. In an eighteenth aspect, a microcarrier of any of aspects 1-17, wherein the microcarrier base is monolithic is provided. In a nineteenth aspect, a method for culturing human embryonic stem cells comprising: contacting the cells with a cell culture medium having microcarriers according to any of claims 1-18; and culturing the cells in the medium is provided. In a twentieth aspect, a method according to aspect 19, wherein the microcarrier base is formed from a mixture of monomers comprising is 2-hydroxyethyl methacrylate, 2-carboxyethyl methacrylate, and (i) methylene bisacrylamide or (ii) dihydroxyethylene bisacrylamide, wherein the mixture of monomers includes (i) 30 to 70 parts per weight of the 2-hydroxyethyl methacrylate; (ii) 20 to 60 parts per weight of the 2-carboxyethyl methacrylate; and (iii) 1 to 15 parts by weight of methylene bisacrylamide or dihydroxyethylene bisacrylamide, and wherein the polypeptide is an RGD-containing polypeptide is provided. In a twenty-first aspect, a method according to aspect 20, wherein the polypeptide is a vitronectin polypeptide is provided. In a twenty-second aspect, a method according to aspect 20 or 21, wherein the mixture of monomers further comprises tetra(ethylene glycol) dimethacrylate, and wherein the combination of the tetra (ethylene glycol)dimethacrylate and the methylene bisacrylamide or the tetra(ethylene glycol)dimethacrylate and the dihydroxyethylene bisacrylamide does not exceed 15 parts by weight of the mixture of monomers is provided.

In the following, non-limiting examples are presented, which describe various embodiments of the microcarriers and methods discussed above.

EXAMPLES

Example 1

Microcarrier Preparation 250 grams of dry toluene and 15 grams of SPAN 85 emulsifier were charged in a 500 milliliter reactor equipped with a thermostatic jacket and bottom drain, dropping funnel, anchor stirrer and inert gas bubbling tube. The temperature of the reactor was set at 40° C. and the mixture was stirred at 500 rpm under argon bubbling for at least 15 min. Then a homogenous mixture containing 22 milliliter of deionized water, 6.3 grams of 2-hydroxyethyl methacrylate, 1.8 grams of 2-carboxyethyl acrylate sodium salt and 1 gram methylene bisacrylamide adjusted at pH 8-10 with NaOH was prepared. 0.5 grams of ammonium persulfate was dissolved in this aqueous solution until a clear and homogeneous solution was obtained. Then this solution was added dropwise by means of the dropping funnel to the stirred toluene/SPAN85 mixture at 40° C. The mixture turned milky rapidly due to the water-in-oil emulsion formation. After 15 min mixing, 100 microliters of tetramethylethylene diamine was added quickly to the stirred emulsion. After 2 hours of reaction, the temperature was cooled down to 20° C. and the microcarriers were withdrawn from the reactor by the bottom drain of the reactor. The microcarriers obtained were thoroughly washed with acetone in order to remove the water insoluble emulsifier and unreacted materials. After drying the microcarrier powder was a white, free flowing powder that could be stored at RT without using special condition.

The microcarriers, without sieving, were viewed under a microscope and appeared to be generally spherical with a narrow size distribution. A representative image is shown in FIG. 1.

Figure 2:
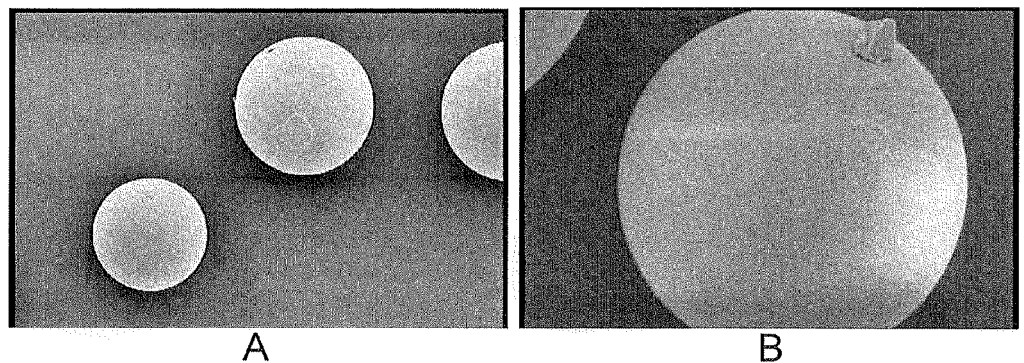
FIGS. 2 A and B are is scanning electron microscope (SEM) images of representative microcarriers prepared according to Example 1.
Figure 3:
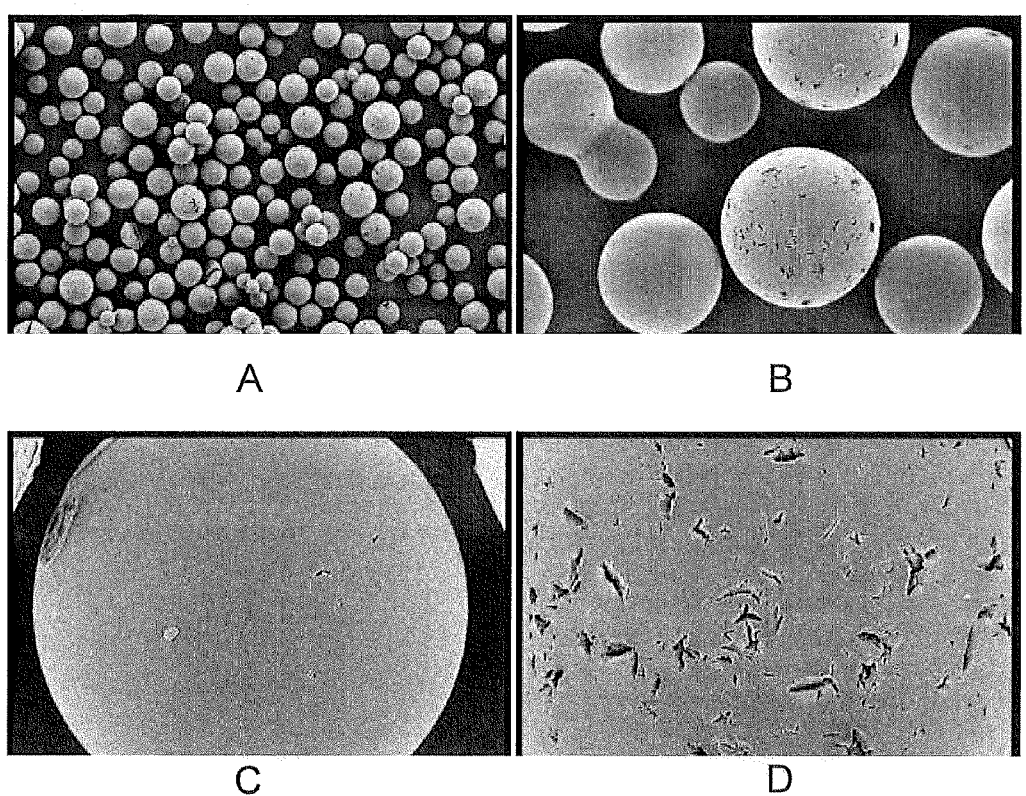
FIG. 3A-D are SEM images of representative microspheres obtained after PBS buffer washing at different magnifications.

The microcarriers were then viewed with the aid of a scanning electron microscope. Briefly, the beads were metalized with 6 nm gold-palladium. Observations were done using Field effect gun scanning electron microscope (ref. LEO1550). The surface of the spherical microcarriers appeared smooth and non-porous (see FIGS. 2A and B showing 500× (FIG. 2A) and 2,000× (FIG. 2B) magnification images, respectively. FIG. 3 shows SEM images of the microspheres obtained after PBS buffer washing at different magnifications.

Figure 4:
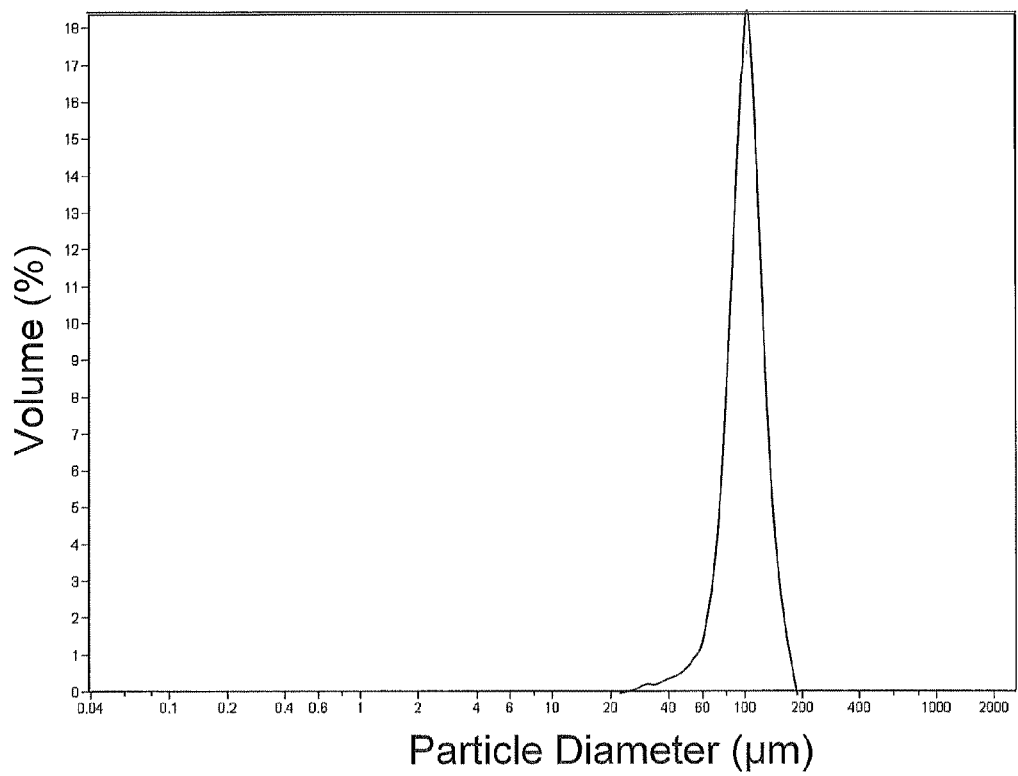
FIG. 4 is a graph of the size distribution of microcarrier particles prepared according to Example 1.

The microcarriers were then subjected to laser diffraction particle size analyzer for determination of size distribution. The analysis was performed using a multi-wavelength Beckman Coulter™ LS 13 320 equipped with an aqueous liquid module and tap water. A graph of the size distribution of the particles is shown in FIG. 4. The particles obtained had a diameter of 101.8 micrometers (+/−24.42 micrometers). Examples 6, 8, and 9 (see below) discuss synthesis of microcarriers having a larger diameters The microspheres were also swelled in water (1.5 cubic centimeters of dry microcarrier in 20 milliliters of water). The microspheres swelled to a volume of about 4.5 cubic centimeters.

Example 2

Assessment of COOH Content Using Crystal Violet 10 micrograms of dry microcarriers prepared according to Example 1 were suspended in 2 milliliters of deionized water and 10 microliters of 5% wt/v crystal violet aqueous solution was added. After sedimentation, the stained microcarriers were washed with deionized water until a colorless supernatant was obtained. The washed microcarriers were suspended in 2 milliliters deionized water. Uniform distribution of staining was observed (data not shown), suggesting that carboxyl groups were evenly distributed along the surface of the microcarriers.

Example 3

Amine Coupling Assessed with Alexa Fluor™ 488 Coupling 10 micrograms of microcarriers prepared according to Example 1 were weighed in an Eppendorf plastic tube and 900 microliters of water was added to disperse the microcarriers by shaking. Then 100 microliters of 200 mM EDC and 50 mM NHS or Sulfo-NHS at was added. The activation was performed for 30 min. The microcarriers were rinsed with 1 ml deionized water after microcarrier sedimentation by centrifugation. Rinsing was repeated three times. Then the activated microcarriers were suspended in 400 microliters borate buffer pH 9.2 and 100 microliters of 1 mM Alexa Fluor™ 488 from Invitrogen Molecular Probes™ was added. After one hour coupling the microcarriers were collected by centrifugation and rinsed three times with PBS buffer.

Substantial fluorescence was observed with EDC/NHS and sulfo-EDC/NHS amine mediated coupling (data not shown), suggesting that either can be used to conjugate polypeptides to the surface of the microspheres. Sulfo-EDC/NHS resulted in slightly more fluorescence than EDC/NHS.

Example 4

Peptide Grafting

For purposes of proof-of-concept, GRGDS (SEQ ID NO:26) peptide was grafted on microcarriers prepared as described in Example 1, using EDC/Sulfo NHS or EDC/NHS mediated coupling. As described above in the specification, other peptides of interest, such as those containing amino acid sequences potentially recognized by proteins from the integrin family, or leading to an interaction with cellular molecules able to sustain cell adhesion, can be grafted using a similar protocol. Briefly, 10 micrograms of dry microcarriers were weighed in an Eppendorf tube and dispersed in 900 microliters of deionized water. Then 100 microliters of 20 mM EDC and 5 mM sulfo-NHS were added and let undisturbed for 30 min. to activate the carboxylic acid groups. The activated microcarriers were collected by centrifugation and rinsed three times with deionized water. They were then resuspended in 400 microliters borate buffer (pH 9) and 100 microliters 5 mM GRGDS (SEQ ID NO:26) peptide was added and left to react for 1 hour.

The microcarriers were collected by centrifugation and washed three times with 1 ml PBS buffer pH 7.4. Finally, the excess activated ester was deactivated by blocking with 1 ml ethanolamine for 30 minutes. The peptide grafted and blocked microcarriers were collected and rinsed three times with PBS. After rinsing with PBS the microcarriers were rinsed 2 times with 70:30% v/v ethanol/water and stored in this ethanol/water solution before cell culture.

Example 5

Cell Culture on Peptide Grafted Microcarriers

CHO-M1 cells (ATCC #CRL-1984) were grown in F-12 Kaighn's modified medium (Gibco) supplemented with 10% fetal bovine serum (Hyclone) and penicillin/streptomycin. Cells were kept in an incubator at 37° C. with 5% CO2 in a humid atmosphere, medium was changed every 3 days, and cells were trypsinized and diluted when needed to remain below confluency.

Before cell seeding, microcarriers prepared according to Example 4 kept in an ethanol/water solution (70/30) were washed 3 times in HBSS buffer (Gibco). Finally, the microcarriers were suspended in cell culture medium and dispensed in a Corning® ULA plate.

Cells for seeding on microcarriers were collected during their exponential growth phase by tryspination. The cells were counted and washed with HBSS buffer. The cell concentration was adjusted to $10^6$ cells/milliliter, and the cells were dispensed on the microcarriers and incubated for at least 4 hours in an incubator.

Figure 5:
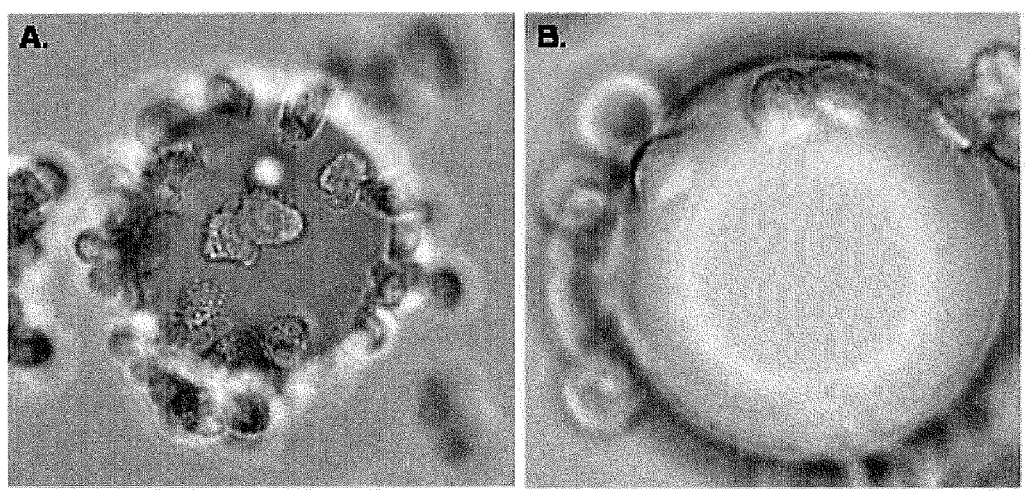
FIGS. 5A and B are is images of CHO-M1 cells adhering on microcarriers grafted with GRGDS peptide.

Cell adhesion on the peptide-grafted microcarriers were observed after the initial 4 hours incubation. Images of CHO-M1 adhering on the carriers are presented in FIG. 5. Image A presents the cells 4 hours after seeding: the rounded shape of the cells is characteristic of the early steps of adhesion. After 16 hours of incubation (image B) the cell spreading on the surface is evident suggesting integrin engagement and focal adhesion formation. Cells at this stage should be transferred to suspension culture vessels for further growth.

Figure 6:
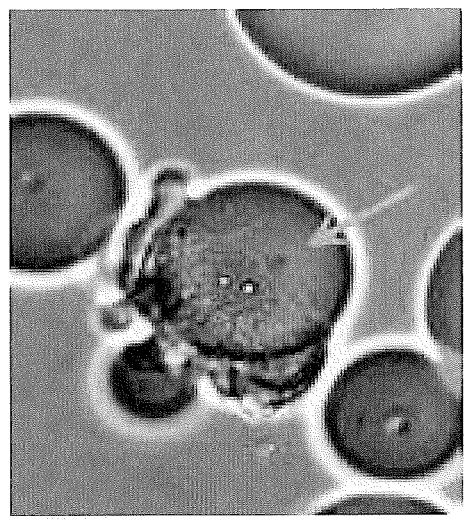
FIG. 6 is an image of HEK293 cells adhering on microcarriers grafted with GRGDS peptide.

HEK293 (ATCC #crl-1573) cells were seeded on microcarriers at different stages of peptides grafting and cultured in DMEM Gibco+10% FBS (Hyclone). Cell adhesion was not observed in the absence of peptide and ethanolamine treatment (not shown). FIG. 6 is an image of HEK293 cells adhering on microcarriers grafted with GRGDS peptide. Briefly HEK293 cells were seeded on microcarriers at different stages of peptides grafting. Cell adhesion was not observed in the absence of peptide and ethanolamine treatment.

Figure 7:
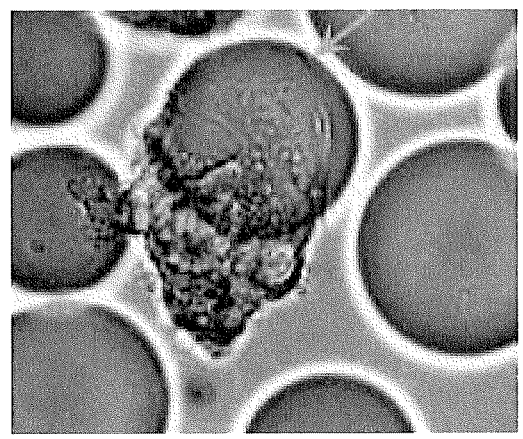
FIG. 7 is an image of MRC5 cells adhering on microcarriers grafted with GRGDS peptide

MRC5 cells (ATCC #CCL-171) were seeded on microcarriers at different stages of peptides grafting and were cultured in DMEM Gibco+10% FBS (Hyclone). Cell adhesion was not observed in the absence of peptide and ethanolamine treatment (not shown). FIG. 7 is an image of MRC5 cells adhering on microcarriers grafted with GRGDS (SEQ ID NO:26) peptide.

These results demonstrate the lack of toxicity of the microcarriers used in these culture conditions.

Example 6

Microcarrier Preparation 250 grams of dry toluene and 15 grams of SPAN 85 emulsifier were charged in a 500 milliliter reactor equipped with a thermostatic jacket and bottom drain, dropping funnel, anchor stirrer and inert gas bubbling tube. The temperature of the reactor was set at 40° C. and the mixture was stirred at 260 rpm under argon bubbling for at least 15 min. Then a homogenous mixture containing 22 milliliter of deionized water, 6.3 grams of 2-hydroxyethyl methacrylate, 1.8 grams of 2-carboxyethyl acrylate sodium salt and 0.5 gram dihydroxyethylene bisacrylamide adjusted at pH 8-10 with NaOH was prepared. 0.5 grams of ammonium persulfate was dissolved in this aqueous solution until a clear and homogeneous solution was obtained. Then this solution was added dropwise by means of the dropping funnel to the stirred toluene/SPAN85 mixture at 40° C. The mixture turned milky rapidly due to the water-in-oil emulsion formation. After 15 min mixing, 100 microliters of tetramethylethylene diamine was added quickly to the stirred emulsion. After 2 hours of reaction, the temperature was cooled down to 20° C. and the microcarriers were withdrawn from the reactor by the bottom drain of the reactor. The microcarriers obtained were thoroughly washed with acetone in order to remove the water insoluble emulsifier and unreacted materials. After drying the microcarrier powder was a white powder that could be stored at 4° C. to prevent agglomeration of the microspheres.

Figure 8:
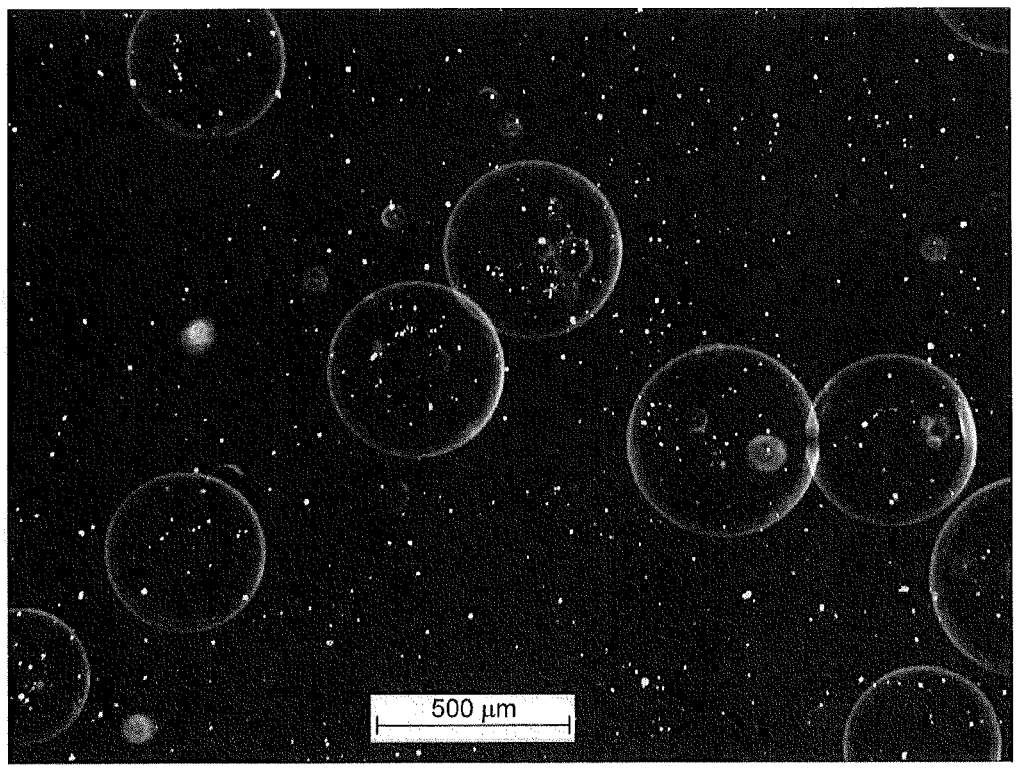
FIG. 8 is a microscopic image of representative microcarriers prepared according to Example 6.

The microcarriers, without sieving, were viewed under a microscope and appeared to be highly spherical with an acceptable size distribution and very high transparency. A representative image is shown in FIG. 8.

Example 7

Vitronectin-Peptide Grafting

Vitronectin-peptide was grafted on microcarriers prepared as described in Example 6, using EDC/Sulfo NHS mediated coupling. Briefly, 10 micrograms of dry microcarriers were weighed in an Eppendorf tube and dispersed in 900 microliters of deionized water. Then 100 microliters of 200 mM EDC and 50 mM sulfo-NHS were added and let undisturbed for 30 minutes to activate the carboxylic acid groups. The activated microcarriers were collected by centrifugation and rinsed three times with deionized water. They were then resuspended in 10 mM vitronectin peptide (ref 341587 (ID #VN) from American peptide Company Inc. CA USA, having an amino acid sequence of Ac-Lys-Gly-Gly-Pro-Gln-Val-Thr-Arg-Gly-Asp-Val-Phe-Thr-Met-Pro-NH$_2$ (SEQ ID NO:24)) in 1000 microliters borate buffer pH 9.2 was added and left to react for 2 hours. The microcarriers were collected by centrifugation and washed three times with 1 ml PBS buffer pH 7.4. Finally, the excess activated ester was deactivated by blocking with 1 ml ethanolamine for 30 minutes. The peptide grafted and blocked microcarriers were collected and rinsed three times with PBS. After rinsing with PBS the microcarriers were rinsed 2 times with 70:30% v/v ethanol/water and stored in this ethanol/water solution before cell culture.

Example 8

RGE-Peptide Grafting

The same procedure as described in Example 7 was reproduced except that RGE-peptide (ref 348454 (ID #RGE) from American peptide Company Inc. CA USA, having amino acid sequence Ac-Gly-Arg-Gly-Glu-Ser-Pro-Ile-Ile-Lys-NH$_2$ (SEQ ID NO:25)) was utilized instead of the vitronectin peptide from Example 7. These microcarriers grafted with a peptide containing a RGE core were used as a negative control.

Example 9

HT1080 Cell Culture on Vitronectin-Peptide and RGE-Peptide Grafted Microcarriers HT-1080 cells (ATCC #CCL-121) were grown in IMDM medium (Gibco) with 10% fetal bovine serum (Hyclone).

Figure 9:
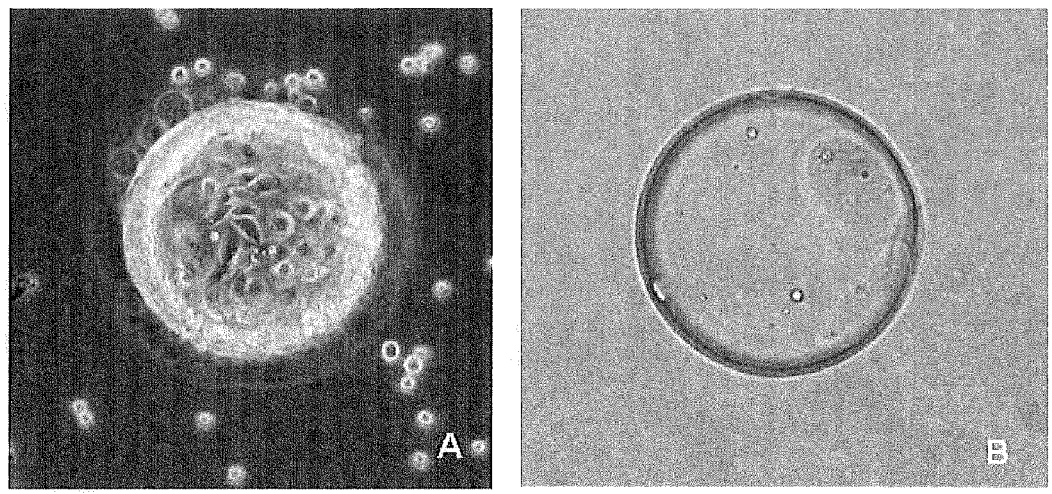
FIGS. 9A and B are is a phase contrast microscopy image of HT1080 cells adhered to a vitronectin polypeptide (A) and an RGE polypeptide (B) grafted to microcarriers, as discussed in Examples 7 and 8, respectively.

For adhesion assays, 10 mg of peptide-grafted microcarriers from example 7 and 8 were washed in D-PBS, resuspended in serum free culture medium and transferred to 24 wells multiwell plates. HT1080 cells were trypsinized, counted and 500,000 cells were mixed with the beads previously prepared. Plates were incubated 1 hour at 37° C. and cell adhesion was observed using phase contrast microscopy as shown in FIG. 9. FIG. 9A shows cells growing on microcarriers having a VN sequence. FIG. 9B shows cell culture with microcarriers with an RGE peptide sequence. Comparison of image A and B reveals that cell adhesion is specific to the RGD core of the vitronectin peptide.

Example 10

Microcarrier Preparation

The same procedure as in Example 1 was reproduced except that stirring speed was 260 rpm. An average particle size of 330 μm was observed (see FIG. 10).

Example 11

Microcarrier Preparation

The same procedure as in Example 1 was reproduced except that stirring speed was 300 rpm. An average particle size of 210 μm was observed (see FIG. 10).

Example 12

Microcarrier Preparation (μHG07)

200 grams of dry toluene and 15 grams of SPAN 85 emulsifier were charged in a 500 milliliter reactor equipped with a thermostatic jacket and bottom drain, dropping funnel, anchor stirrer and inert gas bubbling tube. The temperature of the reactor was set at 40° C. and the mixture was stirred at 260 rpm under argon bubbling for at least 15 min. Then a homogenous mixture containing 10 milliliter of deionized water, 3.1 grams of 2-hydroxyethyl methacrylate, 5.0 grams of 2-carboxyethyl acrylate, 0.15 gram methylene bisacrylamide, 0.40 gram tetraethyleneglycol dimethacrylate and 1 ml ethanol was prepared. The pH was adjusted at pH 8-9 by adding dropwise about 4.45 gram 10M sodium hydroxide. Then, 0.63 grams of ammonium persulfate was dissolved in this aqueous solution until a clear and homogeneous solution was obtained. Then this solution was bubbled for 1 minute with dry argon and added drop wise by means of the dropping funnel to the stirred toluene/SPAN85 mixture at 40° C. After 15 min mixing, 100 microliters of tetramethylethylene diamine was added quickly to the stirred emulsion. After 4 hours of reaction, the temperature was cooled down to 20° C. and the microcarriers were withdrawn from the reactor by the bottom drain of the reactor. The microcarriers obtained were thoroughly washed with acetone in order to remove the surfactant and unreacted materials. The beads were swelled in water for 2 hours and wet-sieved using 100, 200 and 400 μm nylon mesh sieve. After air drying the sieved microcarrier having size between 200 and 400 μm was used for further peptide conjugation as described below.

Example 13

Vitronectin-Peptide Grafting

Vitronectin-peptide was conjugated to microcarriers prepared according to Example 12 using EDC/NHS mediated coupling. Briefly, 10 micrograms of dry microcarriers from Example 12 were weighed in an Eppendorf tube and dispersed in 900 microliters of deionized water. Then 100 microliters of 200 mM EDC and 50 mM NHS were added and let undisturbed for 30 minutes to activate the carboxylic acid groups. The activated microcarriers were collected by centrifugation and rinsed three times with deionized water. Then 1000 microliters of 2.5 mM vitronectin peptide (ref 341587 (ID #VN) from American peptide Company Inc. CA USA, having an amino acid sequence of Ac-Lys-Gly-Gly-Pro-Gln-Val-Thr-Arg-Gly-Asp-Val-Phe-Thr-Met-Pro-NH$_2$ (SEQ ID NO:24)) in borate buffer pH 9.2 was added and the suspension left to react for 30 min, the tube being shaked every 10 minutes. The microcarriers were collected by centrifugation and washed three times with 1 ml PBS buffer pH 7.4. Finally, the excess activated ester was deactivated by blocking with 1 ml 1 M ethanolamine pH 8.4 for 30 minutes. The peptide grafted and blocked microcarriers were collected and rinsed three times with PBS. After rinsing with PBS the microcarriers were rinsed 2 times with 70:30% v/v ethanol/water and stored in this ethanol/water solution before cell culture. These microcarriers are referred herein as μHG07.

Example 14

Microcarrier Preparation (μHG14)

200 grams of dry toluene and 15 grams of SPAN 85 emulsifier were charged in a 500 milliliter reactor equipped with a thermostatic jacket and bottom drain, dropping funnel, anchor stirrer and inert gas bubbling tube. The temperature of the reactor was set at 40° C. and the mixture was stirred at 330 rpm under argon bubbling for at least 15 min. Then a homogenous mixture containing 10 milliliter of deionized water, 3.1 grams of 2-hydroxyethyl methacrylate, 5.0 grams of 2-carboxyethyl acrylate, 0.8 grams of glycerol 1,3-diglycerolate diacrylate was prepared. The pH was adjusted at pH 8-9 by adding dropwise about 4.46 gram 10M sodium hydroxide. Then, 0.63 grams of ammonium persulfate was dissolved in this aqueous solution until a clear and homogeneous solution was obtained. Then this solution was bubbled for 1 minute with dry argon and added drop wise by means of the dropping funnel to the stirred toluene/SPAN85 mixture at 40° C. After 15 min mixing, 150 microliters of tetramethylethylene diamine was added quickly to the stirred emulsion. After 3 hours of reaction, the temperature was cooled down to 20° C. and the microcarriers were withdrawn from the reactor by the bottom drain of the reactor. The microcarriers obtained were thoroughly washed with acetone in order to remove the surfactant and unreacted materials. The beads were swelled in water for 2 hours and wet-sieved using 100, 200 and 400 μm nylon mesh sieve. After air drying the sieved microcarrier having size between 200 and 400 µm was used for peptide conjugation accordingly to the protocol from example 13.

Example 15

Cell Adhesion Assays Using HT1080 Cells

For adhesion assays, 5 mg of VN peptide-grafted microcarriers from Example 13 were washed in D-PBS, saturated with bovine serum albumin (BSA), resuspended in serum free culture medium and transferred to 24 wells multiwell ultralow attachment (ULA) plates.

HT1080 human fibrosarcoma cells (ATCC #CCL-121) were grown in Iscove's Modified Dulbecco's Medium (IMDM) (Gibco) supplemented with 10% fetal bovine serum (FBS) and penicillin streptomycin antibiotics. Cells were kept in an incubator at 37° C., in a humid atmosphere with 5% $CO_2$. Cells were split as needed by trypsinization before they reached confluency.

HT1080, cells were trypsinized washed and counted, and 500,000 cells in serum free medium were mixed with the beads previously prepared. Plates were incubated 2 hours at 37° C. and cell adhesion was observed using phase contrast microscopy. When quantification was needed, the preparation was fixed using 3.7% formaldehyde in PBS and images of the cells.

Figure 11:
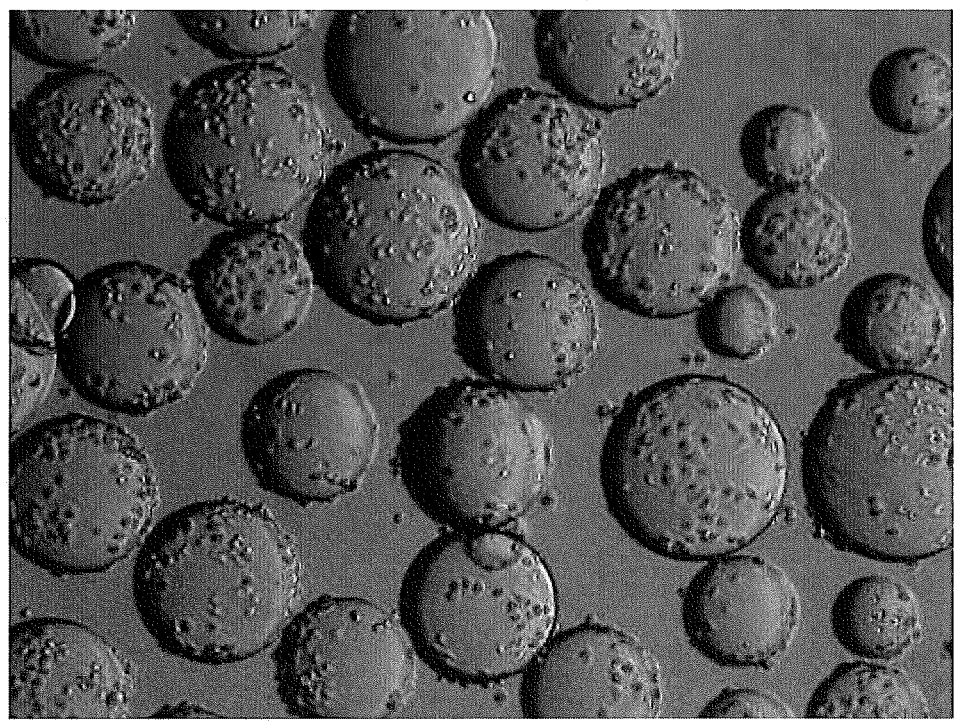
FIG. 11 is a phase contrast microscopy image illustrating HT1080 adhesion after 2 hours incubation on microcarriers.

A representative image of HT1080 cells adhered to µHG07 microcarriers is depicted in FIG. 11, which is a phase contrast microscopy image taken two hours after seeding. As briefly discussed above with regard to EXAMPLE 9, no adhesion of HT1080 cells was observed on microcarriers with grafted RGE polypeptide (µHG0xRGE), but was observed on VN peptide grafted microcarriers, indicating that the cell binding is peptide-specific and that little to no non-specific binding to the microcarrier base occurs (see FIG. 9).

Figure 12:
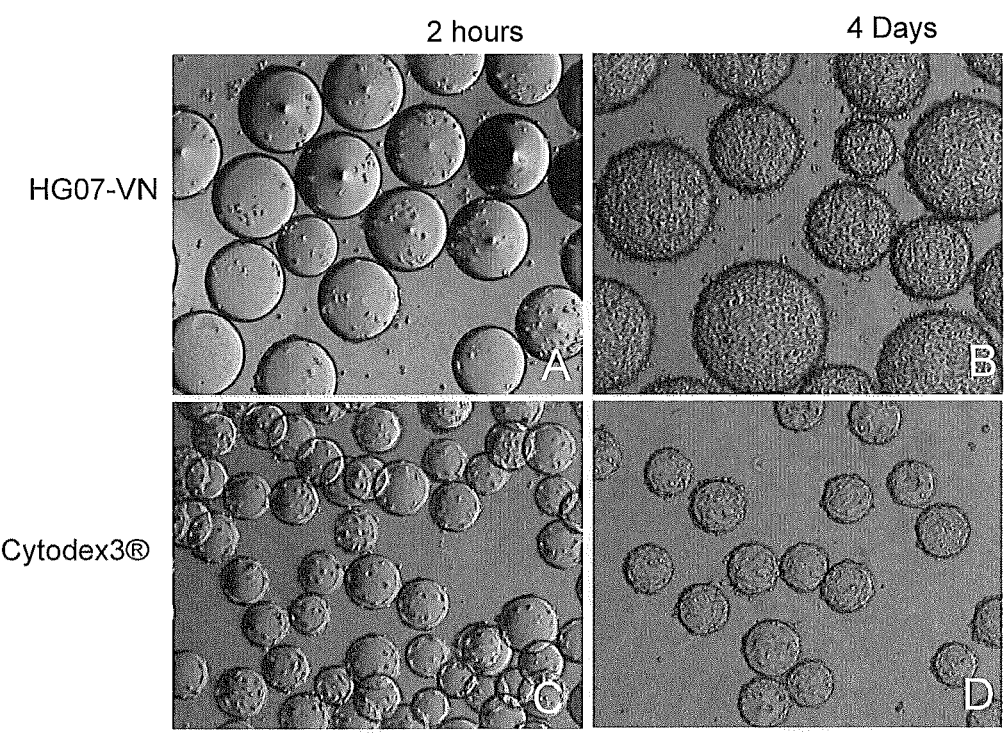
FIGS. 12A-D are a series of phase contrast microscopy image illustrating HT1080 cell adhesion and growth after 2 hours and 4 days in spinner flask on VN grafted microcarriers (FIGS. 12A and B) prepared in accordance with the teachings presented herein or on comparative CYTODEX®3 microcarriers (FIGS. 12C and D).

The ability of the anchorage-dependent HT1080 cells to bind and expand on pHG0X-VN microcarriers series (i.e., those prepared in the Examples presented herein) and to remain bound and grow on microcarriers under stirred culture conditions was examined and compared to CYTODEX® 1 microcarriers (GE Healthcare Biosciences AB Ltd), which are positively charged and are believe to support non-specific binding of anchorage-dependent cells or other commercially available carriers including cytodex3 and SOLOHILL® PRONECTIN® F carriers. Briefly, 100 mg of peptide-grafted microcarriers, or commercially available microcarriers (CYTODEX® 1, CYTODEX® 3, SOLOHILL® PRONECTIN® F) were washed in D-PBS, resuspended in culture medium and transferred to a 125 mL spinner flask (Corning, Inc.). HT1080 cells were trypsinized and counted, and 2.500,000 cells were mixed with the beads previously prepared. After an initial 2 hour adhesion period in a final medium volume of 10 mL without agitation, the medium volume was adjusted to 30 mL and the agitation was setup to 15 minutes every hour. Samples were collected daily and evaluated by phase contrast microscopy. As shown in FIG. 12, HT1080 cells adhered to and expanded on µHG0X-VN microcarriers as well as, or better than, on CYTODEX® 3 beads. µHG07-VN in particular allowed the highest expansion rate. The phase contrast images in FIG. 12 were taken 2 hours, and 4 days after seeding the cells on the µHG07-VN microcarriers.

Figure 13:
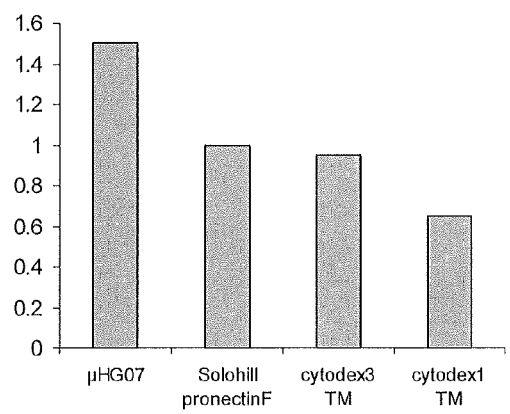
FIG. 13 is a graph of cell growth on different types of microcarriers, as well as reported growth on commercial SOLOHILL® PRONECTIN®F microcarriers. For all conditions cells were grown in spinner flask for 4 days under intermittent stirring.

After 4 to 5 days, cell-bearing carriers were collected by centrifugation, washed in PBS buffer, and the cells were harvested by trysinization. The number of living cells was determined by counting with a Malassez cell after trypan blue exclusion test. The results are presented in FIG. 13, where the final cell number is reported to the growth measured on ProF microcarriers. As shown in FIG. 13, the anchorage dependent HT1080 cells grew better on the µHG07 microcarriers than on the CYTODEX® 1, CYTODEX® 3, and ProF microcarriers.

The results presented herein show that hydrogel microcarriers can support attachment and growth of anchorage-dependent cells, such as HT1080 cells, in a peptide-specific manner in serum free conditions. The binding of the cells to such microcarriers is sufficient to support culture under stirred conditions. Further, the cells appear to attach and grow better on such microcarriers than on other commercially available microcarriers.

Example 16

Adhesion of Pluripotent Mouse Embryonic Stem Cells

For long term adhesion assays, 5 mg of VN peptide-grafted microcarriers, microcarriers were washed in D-PBS, resuspended in serum free culture medium (mTeSR, StemCell Technologies) and transferred to 24 wells multiwell ULA plates.

ES-D3 pluripotent mouse stem embryonic stem cells (ATCC #CRL-11632) were grown in DMEM medium supplemented with 15% FBS and 0.1 mM beta-mercaptoethanol as recommended by ATCC. Cells were routinely grown on MATRIGEL® coated plates, and trypsinized and diluted before they reach confluency.

Figure 14:
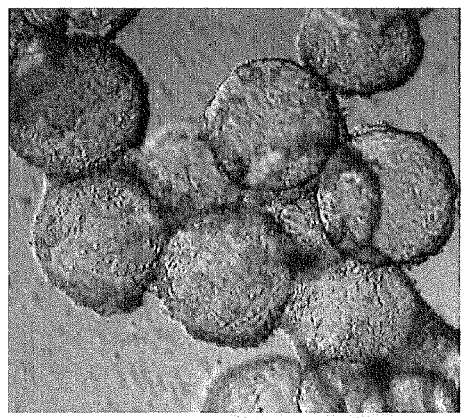
FIG. 14 is a phase contrast microscopy image of ES-D3 mouse pluripotent embryonic stem cells adhesion and growth after 48 hours on peptide grafted microcarriers in serum free conditions and in the presence of 10 µM of Y27632 ROCK kinase inhibitor.

ES-D3 cells were trypsinized, washed and counted. $1\times10^6$ cells were resuspended in mTeSR serum free medium, mixed with the beads previously prepared as described in example 12. Plates were incubated for 48 hours at 37° C., and cell adhesion was observed at 48 hours using phase contrast microscopy (see FIG. 14). Pluripotent mouse embryonic stem cells are able to adhere nicely to the microcarriers tested. We observe that, despite the lack of agitation, the tendency of the microcarriers to form aggregates is limited.

Cell pluripotency was investigated at the end of the experiment by dosing the activity of alkaline phosphatase, an enzyme specifically expressed by pluripotent embryonic stem cells. The results, which are presented in FIG. 15, indicate that the cells pluripotency is maintained as expected in a way comparable to what is observed on the positive control (CYTODEX® 3). STO mouse fibroblasts (ATCC #CRL-1503) grown on TCT as recommended by ATCC are used as a negative control, as expected cells are not pluripotent and do not express alkaline phosphatase.

Figure 15:
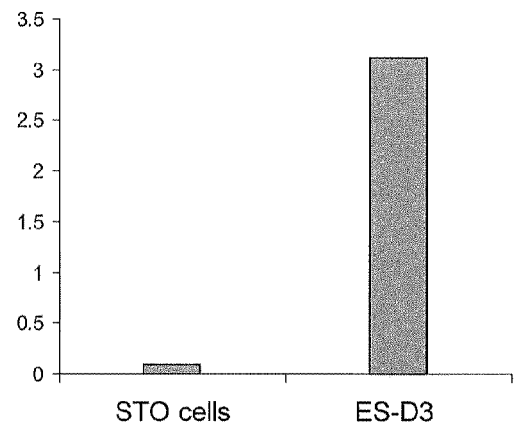
FIG. 15 is a graph showing the alkaline phosphatase activity in cell extracts performed at the end of the experiment in Example 15, where STO mouse fibroblasts were used as a negative control.
Figure 16:
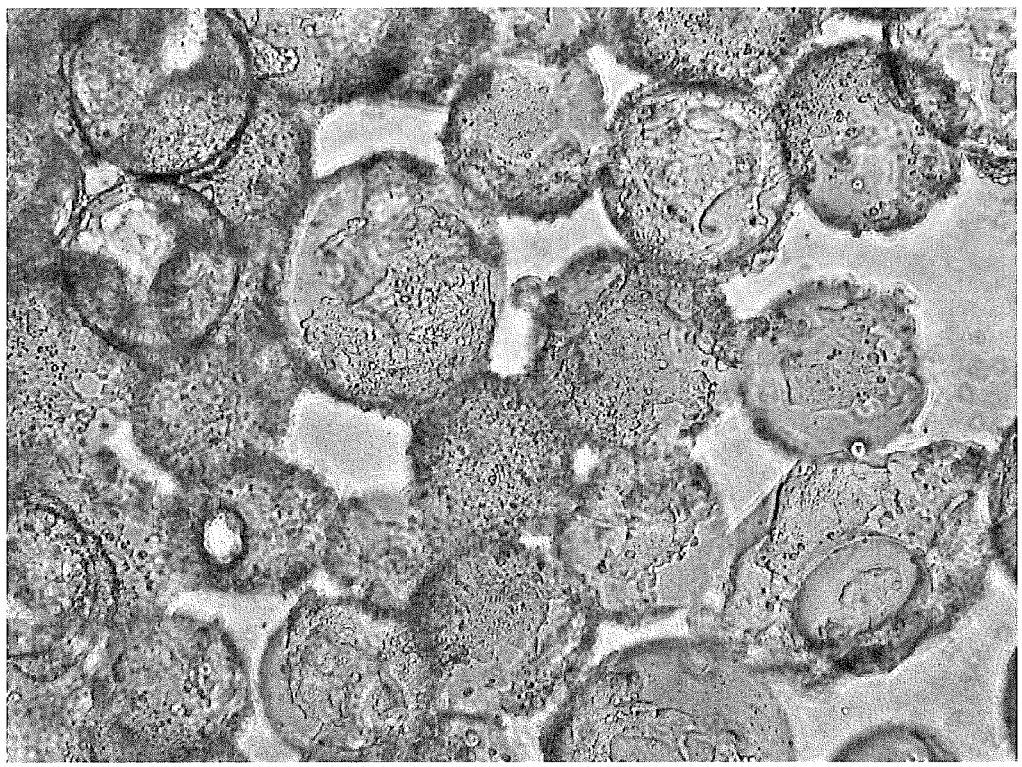
FIG. 16 is a phase contrast microscopy image showing ES-D3 mouse embryonic stem cells adhering on the microcarriers of Example 14 (µHG14). The cells were incubated for 18 hours with the beads in mTeSR1 serum free medium

ES-D3 mESC were also able to adhere on the microcarriers prepared as in Example 14 as illustrated in FIG. 15.

Those results support the suggestion that the microcarriers described herein will support culture of pluripotent stem cells, such as human embryonic stem cells.

Example 16

Adhesion and Expansion of Human Embryonic Stem Cells

BG01V/hOG cells (Invitrogen) were maintained on MATRIGEL® coated TCT 75 Flask (Corning) in serum free mTeSR1 medium containing 50 µg/ml Hygromycin B (STEMCELL Technologie). Daily medium changes began after the first 48 h in culture. Cells were passaged every 5 to 6 days using collagenase IV (Invitrogen) and mechanical scraping.

For the assay, aggregate colonies were harvested and resuspended in fresh mTeSR1 serum free medium. Cells were seeded to the 24 wells Corning Ultra low attachment microplate (1.5×105 cells per cm2) containing the VN-peptide grafted μHG07 microcarriers, prepared as described above, or CYTODEX® 3 microcarrier available from GE Healthcare as a comparative example. The volume was adjusted to 600 microliters with culture medium. Cells were allowed to attach to the microcarriers for 48 h without agitation. Two days after seeding, cellular attachment and spreading was assessed using Ziess Axiovert 200M inverted microscope.

Figure 17:
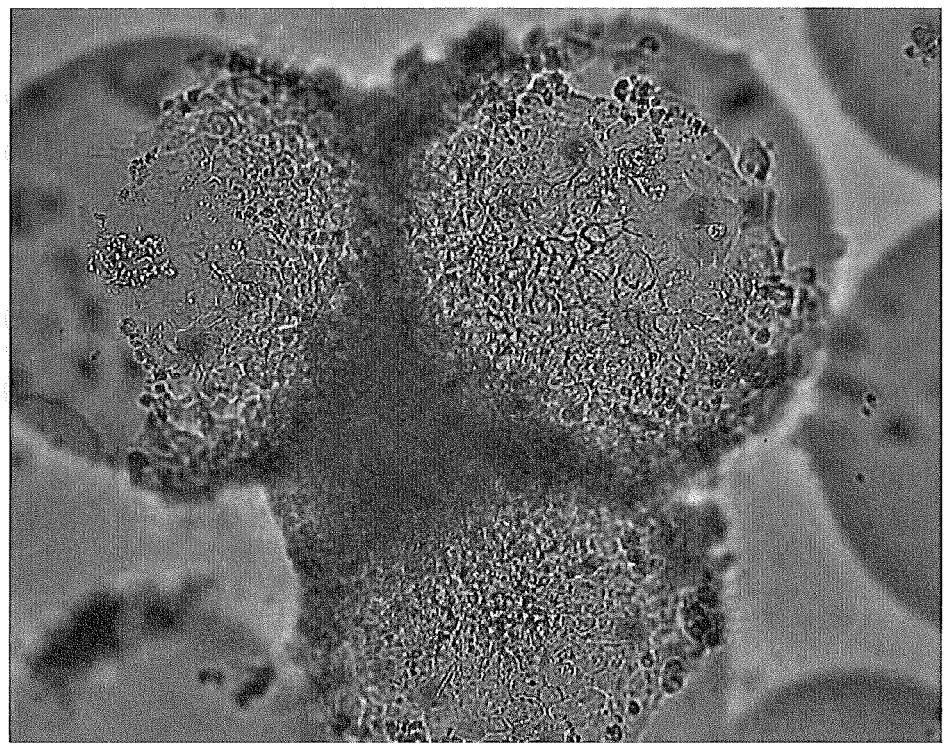
FIG. 17 is a microscopy image illustrating BG01V cells attachment on peptide grafted microcarriers 5 days after seeding.

As shown in FIG. 17, one can observe a nice spreading of BG01V/hOG cell colonies on μHG07-VN beads. On Cytodex 3 beads the cells were not able to adhere and instead formed floating embryonic bodies.

Figure 18:
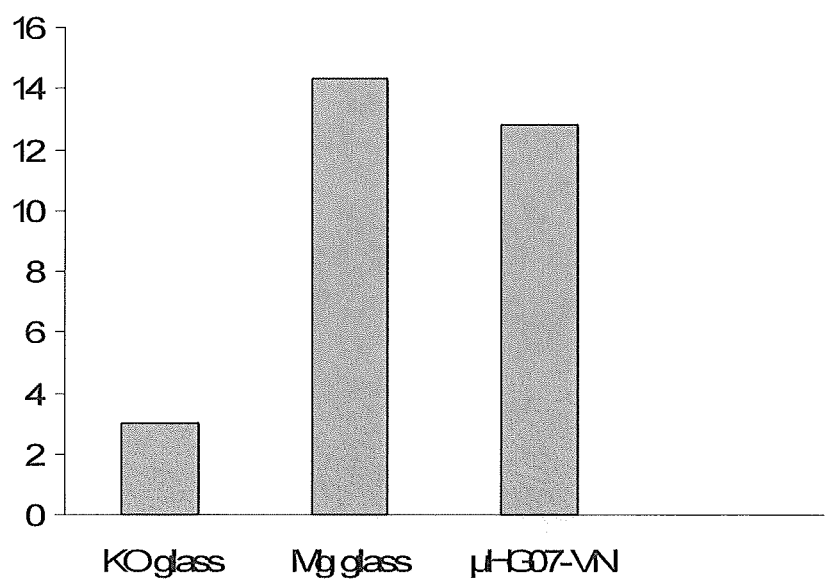
FIG. 18 is a graph presenting the result of BG01V cell growth in stirred conditions on different types of microcarriers. MATRIGEL® (Mg) coated glass carriers are used as a gold standard, non coated (KO) glass beads are used as a negative control.

For stirred culture, $5 \times 10^6$ cells were seeded as described previously on 50 mg of microcarriers in a spinner flask in a final volume of 15 mL mTeSR1 medium, cells were incubated for 2 days without agitation, and then cultures were stirred gently 15 minutes every 2 hours. 80% of the medium was changed daily beginning after 48 hours. At day 5 microcarriers were collected cells were recovered by trypsination and counted using the trypan blue exclusion method. The results obtained are presented in FIG. 18, which show that the cell growth observed on hydrogel microcarriers is comparable to what is observed on MATRIGEL® coated glass beads, used as a gold standard. No significant growth is observed on non coated glass beads used as a negative control. This experiment demonstrates the suitability of microcarriers as described herein to support the growth of undifferentiated human embryonic stem cells in stirred conditions for several days.

Example 17

Comparison of Various Microcarriers to Support Cell Adhesion

Microcarriers were formed from a variety of monomers at differing concentrations and the physical properties and ability various cells to attach to the microcarriers were examined. The microcarrier bases were prepared as generally described in the previous Examples and vitronectin polypeptide was conjugated to the microcarrier base to form the microcarrier for cell culture as described in prior Examples. The swelling factor and equilibrium water content (EWC) of the microcarrier base. The peptide density of the resulting microcarrier was evaluated as described in the previous Examples. The ability of HT1080 cells, ESD3 cells, and BG01 V/Hog human embryonic stem cells to attach to the microcarriers under cell culture conditions as described in the previous Examples were also evaluated by microscopic observation.

The monomers employed to form the carious microcarrier bases are listed in Table 1.

TABLE 1

Monomers used to form microcarrier bases

| | μHG07 | μHG12 | μHG10 | μHG11 | μHG14 |
|---|---|---|---|---|---|
| HEMA | 35.84 | 34.6 | 33.37 | 30.44 | 34.83 |
| CEA | 57.8 | 55.8 | 53.82 | 54.35 | 56.18 |
| MBA | 1.74 | 2.46 | 3.23 | 6.52 | 0 |
| TEGDMA | 4.62 | 7.14 | 9.58 | 8.69 | 0 |
| GDGDA | 0 | 0 | 0 | 0 | 8.99 |

The numbers presented in Table 1 represent the amount of monomer employed in grams; HEMA=2-hydrodyethyl methacrylate; CEA=2-carboxyethyl acrylate; MBA=methylene bisacrylamide; TEGDMA=tetra(ethylene glycol)dimethacrylate; GDGDA=glycerol 1,3-diglycerolate diacrylate.

All the microcarrier bases had about 4 milliequivalents of carboxylic acid functional group per gram, yet the polypeptide density varied among the microcarriers even though the processes for conjugating the polypeptide were the same. The amount of crosslinker used correlated with the polypeptide density (see, FIG. 19), with the polypeptide density decreasing with increasing crosslinker %. The specific estimated COOH functionality, weight percent crosslinker and polypeptide density for each microcarrier base is presented in Table 2.

TABLE 2

COOH functionality, crosslinker, and peptide density of microcarriers or microcarrier bases

| | μHG07 | μHG12 | μHG10 | μHG11 | μHG14 |
|---|---|---|---|---|---|
| Estimated COOH (meq/gm) | 4 | 3.9 | 3.74 | 3.78 | 3.9 |
| % wt x-linker | 6.3 | 8.2 | 13 | 15 | 8.99 |
| Peptide loading (nmol/mg) | 153 | 118 | 108 | 59 | 99 |

The ability of the microcarriers to swell and the equilibrium water content of each of the microcarriers was evaluated and the results are presented in Table 3.

TABLE 3

Swelling factor and EWC of microcarrier bases

| | μHG07 | μHG12 | μHG10 | μHG11 | μHG14 |
|---|---|---|---|---|---|
| Swelling factor (ml/gm) | 30 | 15 | 10 | 7 | 16 |
| EWC (%) | 97 | 93 | 90 | 86 | 94 |

The swelling factor and EWC of the resulting microcarriers is considerably higher than the swellable (meth)acrylate layers formed in the examples of copending U.S. patent application Ser. Nos. 12/362,924 and 12/362,974. This is believed to be due to the increased weight percent of the carboxylic acid containing monomer used in the microcarriers described in the present Examples. In copending U.S. patent application Ser. Nos. 12/362,924 and 12/362,974, the swellable (meth)acrylate layers were formed in situ on a substrate. If the EWC were too high, the layer may swell too much and delaminate. However, as the microcarriers described herein are not formed as a layer on a substrate, delamination is not a concern and the EWC can be considerably higher. In many respects, microcarriers with higher EWCs are desirable because they tend to have low stiffness and thus more closely resemple biological tissue stiffness, high transparency due to the high amount of water, and prevent or reduce cell damage during collision in stirred cultures.

The ability of these microcarriers to support attachment of cells varied, as shown in Table 4.

TABLE 4

Ability of cells to attach to microcarriers

|  | μHG07 | μHG12 | μHG10 | μHG11 | μHG14 |
|---|---|---|---|---|---|
| HT1080 attachemnts (static culture) | Good (about 10-15 cells/bead) | Excellent (20+ cells/bead) | Good (about 10-15 cells/bead) | Excellent (20+ cells/bead) | Excellent (20+ cells/bead) |
| ESD3 attachemnt (static culture) | Excellent | Excellent | Excellent | Poor at 24 h, failed at 48 h | Good |
| ESD3 attachement (spinner flask) | Excellent | Good | Good | Failed | Failed |
| BG01V/hOG (static culture) | Good | Good | Good | Good | Not tested |

All of the microcarriers tested were good or excellent with regard to HT1080 cell attachment. In contrast, ESD3 stem cells were observed to attach to only some of the microcarriers. Microcarriers that had a polypeptide density of 100 nmol/mg or more were able to support attachment of ESD3 cells, while those having a polypeptide density of 100 nmol/mg or less were not able to support attachment of ESD3 cells at all or in stirred culture conditions (spinner flask). With regard to human embryonic stem cells, BG01V/hOG, attachment was good to all microcarriers tested. While not tested, the ability of the human embryonic stem cells to the some of microcarriers under stirred conditions may not be as good under stirred conditions. None-the-less, the results presented herein show that a variety of microcarriers as described herein support attachment of a variety of cell types.

Based on the results presented in this Example, it appears that the crosslinker concentration and type can have an impact on the EWC and peptide loading, which may also affect the ability of the microcarrier to support culture of various cell types. Accordingly, the nature and amount of crosslinker, as well of other monomers, can be readily modified to tune the microcarrier to support culture for a desired cell type.

Thus, embodiments of SYNTHETIC MICROCARRIERS FOR CULTURING CELLS are disclosed. One skilled in the art will appreciate that the arrays, compositions, kits and methods described herein can be practiced with embodiments other than those disclosed. The disclosed embodiments are presented for purposes of illustration and not limitation.

What is claimed is:

1. A microcarrier for cell culture, comprising:
   (A) a polymeric microcarrier base formed from copolymerization of a mixture of monomers comprising:
      (i) 30 to 36 parts per weight of an uncharged hydrophilic unsaturated monomer having a hydroxyl group selected from a hydrophilic (meth)acrylate monomer having a hydroxyl group or a hydrophilic (meth)acrylamide monomer having a hydroxyl group,
      (ii) 53 to 58 parts per weight of a hydrophilic carboxylic acid containing unsaturated monomer selected from a carboxylic acid containing (meth)acrylate monomer or a carboxylic acid containing (meth)acrylamide monomer, and
      (iii) 6 to 15 parts by weight of a first hydrophilic multifunctional unsaturated monomer selected from a hydrophilic multifunctional (meth)acrylate monomer or a hydrophilic multifunctional (meth)acrylamide monomer; and
   (B) a polypeptide conjugated to the microcarrier base,
   wherein the microcarrier base, prior to conjugation of the polypeptide, has an equilibrium water content (EWC) of greater than 75% in distilled, deionized water at room temperature, wherein EWC is determined by according to the following formula: EWC(%)=[(Wgel−Wdry)]*100, where Wgel is the weight of the microcarrier base, inclusive of water, after swelling in the deionized water and Wdry is the dry weight of the microcarrier base, and
   wherein the microcarrier base, prior to conjugation of the polypeptide, has pendant carboxylic acid groups of 2 milliequivalents or greater per gram of the microcarrier base.

2. A microcarrier according to claim 1, wherein the uncharged hydrophilic unsaturated monomer having a hydroxyl group is selected from the group consisting of hydroxypropyl methacrylate, 2-hydroxyethyl methacrylate, 2-hydroxyethyl acrylate, glycerol methacrylate, hydroxypropyl acrylate, 4-hydroxybutyl acrylate, N-(hydroxymethyl) acrylamide, N-[Tris(hydroxymethyl)methyl]acrylamide, 3-acryloylamino-1-propanol, N-acrylamido-ethoxyethanol, and N-hydroxyethyl acrylamide.

3. A microcarrier according to claim 1, wherein the uncharged hydrophilic unsaturated monomer having a hydroxyl group is 2-hydroxyethyl methacrylate.

4. A microcarrier according to claim 1 wherein the hydrophilic carboxylic acid containing unsaturated monomer is selected from the group consisting of 2-carboxyethyl acrylate, acrylic acid, methacrylic acid, 2-carboxyethyl acrylamide, and acrylamidoglycolic acid.

5. A microcarrier according to claim 4, wherein the hydrophilic carboxylic acid containing unsaturated monomer is 2-carboxyethyl acrylate.

6. A microcarrier according to claim 1, wherein the first hydrophilic multifunctional unsaturated monomer is selected from the group consisting of N,N'methylenebisacrylamide, N,N'(1,2dihydroxyethylene)bisacrylamide, polyethylene glycol di(meth)acrylate, triglycerol diacrylate, propylene glycol glycerolate diacrylate, trimethylolpropane ethoxylate triacrylate, and glycerol 1,3-diglycerolate diacrylate.

7. A microcarrier according to claim 6, wherein the first hydrophilic multifunctional unsaturated monomer is selected from the group consisting of methylene bisacrylamide and dihydroxyethylene bisacrylamide.

8. A microcarrier according to claim 1, wherein the mixture of monomers further comprises a second multifunctional unsaturated monomer selected from a multifunctional unsaturated (meth)acrylate monomer or a multifunctional unsaturated (meth)acrylamide monomer.

9. A microcarrier according to claim 8, wherein the second multifunctional unsaturated monomer is less hydrophilic than the first hydrophilic multifunctional unsaturated monomer.

10. A microcarrier according to claim 9, wherein the second multifunctional unsaturated monomer is tetra(ethylene glycol) dimethacrylate.

11. A microcarrier according to claim 8, wherein the first hydrophilic multifunctional unsaturated monomer and the second multifunctional unsaturated monomer together do not exceed 15 parts by weight of the mixture of monomers.

12. A microcarrier according to claim 11, wherein the first hydrophilic multifunctional unsaturated monomer consists essentially of methylene bisacrylamide or dihydroxyethylene bisacrylamide, the second hydrophilic multifunctional unsaturated monomer consists essentially of tetra(ethylene glycol) dimethacrylate, and wherein the combination of the tetra (ethylene glycol)dimethacrylate and the methylene bisacrylamide or the tetra(ethylene glycol)dimethacrylate and the dihydroxyethylene bisacrylamide does not exceed 15 parts by weight of the mixture of monomers.

13. A microcarrier according to claim 1, wherein the polypeptide is an RGD-containing polypeptide.

14. A microcarrier according to claim 1, wherein the microcarrier has greater than 100 nmol conjugated polypeptide per milligram of microcarrier base.

15. A method for culturing human embryonic stem cells comprising:
    contacting the cells with a cell culture medium having microcarriers according to claim 1; and
    culturing the cells in the medium.

16. A method for culturing human embryonic stem cells comprising:
    contacting the cells with a cell culture medium having microcarriers according to claim 10, wherein the uncharged hydrophilic unsaturated monomer having a hydroxyl group is selected from the group consisting of hydroxypropyl methacrylate, 2-hydroxyethyl methacrylate, 2-hydroxyethyl acrylate, glycerol methacrylate, hydroxypropyl acrylate, 4-hydroxybutyl acrylate, N-(hydroxymethyl)acrylamide, N-[Tris(hydroxymethyl)methyl]acrylamide, 3-acryloylamino-1-propanol, N-acrylamido-ethoxyethanol, and N-hydroxyethyl acrylamide and wherein the hydrophilic carboxylic acid containing unsaturated monomer is selected from the group consisting of 2-carboxyethyl acrylate, acrylic acid, methacrylic acid, 2-carboxyethyl acrylamide, and acrylamidoglycolic acid; and
    culturing the cells in the medium.

17. A microcarrier according to claim 1,
    wherein the microcarrier base is formed from a mixture of monomers comprising
    2-hydroxyethyl methacrylate,
    2-carboxyethyl acrylate, and
    (i) methylene bisacrylamide or (ii) dihydroxyethylene bisacrylamide, and
    wherein the polypeptide is an RGD-containing polypeptide.

18. A microcarrier according to claim 1, wherein the uncharged hydrophilic unsaturated monomer having a hydroxyl group is a monomer according to Formula (I) or Formula (II):

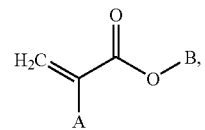

(I)

where A is H or methyl, and where B is C1-C6 straight or branched chain alcohol or ether. In some embodiments, B is C1-C4 straight or branched chain alcohol; or

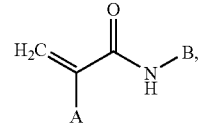

(II)

where A is hydrogen or methyl, and where B is C1-C6 straight or branched chain alcohol or ether.

19. A microcarrier according to claim 1, wherein the hydrophilic carboxylic acid containing unsaturated monomer is a monomer according to Formula (III) or Formula (IV):

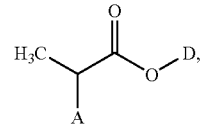

(III)

where A is hydrogen or methyl, and where D is C1-C6 straight or branched chain alkyl substituted with a carboxyl group (—COOH); or

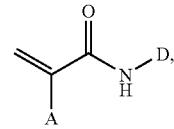

(IV)

where A is hydrogen or methyl, and where D is C1-C6 straight or branched chain alkyl substituted with a carboxyl group (—COOH).

20. A microcarrier according to claim 1, wherein the microcarrier base, prior to conjugation of the polypeptide, has pendant carboxylic acid groups of 3 milliequivalents or greater per gram of the microcarrier base.

21. A microcarrier according to claim 1, wherein the microcarrier base, prior to conjugation of the polypeptide, has pendant carboxylic acid groups of about 4 milliequivalents or greater per gram of the microcarrier base.

* * * * *